US006454752B1

(12) United States Patent
Huang et al.

(10) Patent No.: US 6,454,752 B1
(45) Date of Patent: Sep. 24, 2002

(54) PRE-FASTENED ADJUSTABLE MECHANICAL FASTENER GARMENT

(75) Inventors: Yung Hsiang Huang, Appleton; Thomas Harold Roessler, Menasha; Gary Lee Travis, Oshkosh; Paul Theodore VanGompel, Hortonville, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/527,776

(22) Filed: Mar. 17, 2000

(51) Int. Cl.[7] .................................................. A61F 13/15
(52) U.S. Cl. ............. 604/389; 604/385.03; 604/385.01; 604/387
(58) Field of Search .......................... 604/385.03, 389, 604/385.01, 387

(56) References Cited

U.S. PATENT DOCUMENTS

| | | |
|---|---|---|
| 1,079,479 A | 11/1913 | Earnshaw |
| 1,485,001 A | 2/1924 | Willis |
| 1,657,909 A | 1/1928 | Abramovich |
| 1,705,194 A | 3/1929 | Marinsky |
| 1,762,468 A | 6/1930 | Brewer |
| 1,963,334 A | 6/1934 | Neilson |
| 2,201,255 A | 5/1940 | Wilson, Jr. |
| 2,242,977 A | 5/1941 | Marcos |
| 2,475,175 A | 7/1949 | Cadous |
| 2,477,914 A | 8/1949 | Webb |
| 2,545,761 A | 3/1951 | Brink |
| 2,570,963 A | 10/1951 | Mesmer |
| 2,630,120 A | 3/1953 | Nielson |
| 2,630,806 A | 3/1953 | Kiscaden |
| 2,743,725 A | 5/1956 | Matthews |
| 2,801,632 A | 8/1957 | Burner et al. |
| 2,808,831 A | 10/1957 | Winslett |

(List continued on next page.)

FOREIGN PATENT DOCUMENTS

| | | |
|---|---|---|
| AU | 667899 | 4/1996 |
| CA | 2096672 | 11/1993 |
| CA | 2103992 A1 | 2/1994 |
| CA | 2187021 A1 | 10/1995 |
| CA | 2187366 A1 | 10/1995 |
| EP | 0 206 208 B1 | 12/1986 |
| EP | 0 217 032 A2 | 4/1987 |

(List continued on next page.)

OTHER PUBLICATIONS

Derwent World Patent Database abstract of FR 2762507 A1: Description of RAHALA, "Baby's Disposable Nappy".
Derwent World Patent Database abstract of JP 6–063076 A: Description of Kao Corp. (Kaos), "Throw Away Diaper or Nappy".

(List continued on next page.)

Primary Examiner—Rodney M. Lindsey
Assistant Examiner—Angela J Grayson
(74) Attorney, Agent, or Firm—Jeffrey B. Curtin; John L. Brodersen

(57) ABSTRACT

A pant-like, prefastened, refastenable, disposable absorbent article includes a pair of fasteners which provide refastenable side seams and at least one waist size adjustment means. The prefastened absorbent article defines a pair of laterally opposed side edges and a pair of longitudinally opposed waist edges. The fasteners are permanently attached to the side edges of one of the waist edges and engage the side edges of the opposed waist edges to form the refastenable side seams defining a waist opening and a pair of leg openings in the prefastened absorbent article. The fasteners are further configured to provide a waist size adjustment means. The waist size adjustment means allows the wearer or the caregiver to reduce or increase the waist perimeter dimension of the prefastened absorbent article to conform the article to the wearer's body after the absorbent article is positioned on the wearer by releasably engaging the waist size adjustment means to the exterior surface of the prefastened absorbent article.

42 Claims, 11 Drawing Sheets

U.S. PATENT DOCUMENTS

| | | |
|---|---|---|
| 2,830,589 A | 4/1958 | Doner |
| 2,833,282 A | 5/1958 | Moore |
| 2,910,982 A | 11/1959 | Woodward |
| 2,931,361 A | 4/1960 | Sostrin |
| 3,039,466 A | 6/1962 | Wilson |
| 3,077,193 A | 2/1963 | Mann |
| 3,610,244 A | 10/1971 | Jones, Sr. |
| 3,638,651 A | 2/1972 | Torr |
| 3,653,381 A | 4/1972 | Warnken |
| 3,825,006 A | 7/1974 | Ralph |
| 3,882,871 A | 5/1975 | Taniguchi |
| 4,024,867 A | 5/1977 | Mesek |
| 4,051,853 A | 10/1977 | Egan, Jr. |
| 4,051,854 A | 10/1977 | Aaron |
| 4,066,081 A | 1/1978 | Schaar |
| 4,074,716 A | 2/1978 | Schaar |
| 4,089,068 A | 5/1978 | Swallow |
| 4,090,516 A | 5/1978 | Schaar |
| 4,205,679 A | 6/1980 | Repke et al. |
| 4,210,143 A | 7/1980 | De Jonckheere |
| 4,315,508 A | 2/1982 | Bolick |
| 4,337,771 A | 7/1982 | Pieniak et al. |
| 4,409,049 A | 10/1983 | Passafiume et al. |
| 4,410,327 A | 10/1983 | Baggaley |
| 4,500,316 A | 2/1985 | Damico |
| 4,515,595 A | 5/1985 | Kievit et al. |
| 4,522,853 A | 6/1985 | Szonn et al. |
| 4,525,407 A | 6/1985 | Ness |
| 4,563,185 A | 1/1986 | Reiter |
| 4,568,341 A | 2/1986 | Mitchell et al. |
| 4,581,772 A | 4/1986 | Smith |
| 4,596,055 A | 6/1986 | Aach et al. |
| 4,598,528 A | 7/1986 | McFarland et al. |
| 4,604,096 A | 8/1986 | Dean et al. |
| 4,610,680 A | 9/1986 | LaFleur |
| 4,610,681 A | 9/1986 | Strohbeen et al. |
| 4,615,695 A | 10/1986 | Cooper |
| 4,617,022 A | 10/1986 | Pigneul et al. |
| 4,619,649 A | 10/1986 | Roberts |
| 4,623,339 A | 11/1986 | Ciraldo et al. |
| 4,630,320 A | 12/1986 | Van Gompel |
| 4,663,220 A | 5/1987 | Wisneski et al. |
| 4,675,918 A | 6/1987 | O'Brien |
| D290,780 S | 7/1987 | Wistrand |
| 4,699,622 A | 10/1987 | Toussant et al. |
| 4,704,116 A | 11/1987 | Enloe |
| 4,726,874 A | 2/1988 | Van Vliet |
| 4,728,326 A | 3/1988 | Gilles |
| 4,743,239 A | 5/1988 | Cole |
| 4,747,846 A | 5/1988 | Boland et al. |
| 4,753,646 A | 6/1988 | Enloe |
| 4,753,650 A | 6/1988 | Williams |
| 4,798,603 A | 1/1989 | Meyer et al. |
| 4,801,485 A | 1/1989 | Sallee et al. |
| 4,808,252 A | 2/1989 | Lash |
| 4,826,499 A | 5/1989 | Ahr |
| 4,850,988 A | 7/1989 | Aledo et al. |
| 4,850,992 A | 7/1989 | Amaral et al. |
| 4,857,067 A | 8/1989 | Wood et al. |
| 4,883,481 A | 11/1989 | Blanchard |
| 4,892,598 A | 1/1990 | Stevens et al. |
| 4,895,569 A | 1/1990 | Wilson et al. |
| 4,904,252 A | 2/1990 | Fitzgerald |
| 4,908,247 A | 3/1990 | Baird et al. |
| 4,909,802 A | 3/1990 | Ahr et al. |
| 4,911,702 A | 3/1990 | O'Leary et al. |
| 4,917,682 A | 4/1990 | Lancaster et al. |
| 4,936,840 A | 6/1990 | Proxmire |
| 4,937,887 A | 7/1990 | Schreiner |
| 4,938,753 A | 7/1990 | Van Gompel et al. |
| 4,944,733 A | 7/1990 | Casale |
| 4,961,736 A | 10/1990 | McCloud |
| 4,964,860 A | 10/1990 | Gipson et al. |
| 4,973,326 A | 11/1990 | Wood et al. |
| 4,988,346 A | 1/1991 | Pfefferkorn |
| 4,998,929 A | 3/1991 | Bjorksund et al. |
| 5,019,072 A | 5/1991 | Polski |
| 5,019,073 A | 5/1991 | Roessler et al. |
| 5,040,244 A | 8/1991 | Tubbs |
| 5,062,839 A | 11/1991 | Anderson |
| 5,066,289 A | 11/1991 | Polski |
| 5,069,678 A | 12/1991 | Yamamoto et al. |
| 5,074,854 A | 12/1991 | Davis |
| 5,087,253 A | 2/1992 | Cooper |
| 5,106,382 A | 4/1992 | Henry |
| 5,106,385 A | 4/1992 | Allen et al. |
| 5,110,403 A | 5/1992 | Ehlert |
| 5,112,326 A | 5/1992 | Quadrini |
| 5,135,522 A | 8/1992 | Fahrenkrug et al. |
| 5,140,757 A | 8/1992 | Terada |
| 5,163,932 A | 11/1992 | Nomura et al. |
| 5,170,505 A | 12/1992 | Rohrer |
| 5,176,668 A | 1/1993 | Bernardin |
| 5,176,670 A | 1/1993 | Roessler et al. |
| 5,176,672 A | 1/1993 | Bruemmer et al. |
| 5,185,011 A | 2/1993 | Strasser |
| 5,186,779 A | 2/1993 | Tubbs |
| 5,187,817 A | 2/1993 | Zolner |
| 5,192,606 A | 3/1993 | Proxmire et al. |
| 5,226,992 A | 7/1993 | Morman |
| 5,236,430 A | 8/1993 | Bridges |
| 5,242,436 A | 9/1993 | Weil et al. |
| 5,246,433 A | 9/1993 | Hasse et al. |
| 5,275,590 A | 1/1994 | Huffman et al. |
| 5,300,057 A | 4/1994 | Miller et al. |
| 5,304,162 A | 4/1994 | Kuen |
| 5,312,387 A | 5/1994 | Rossini et al. |
| 5,340,431 A | 8/1994 | Terada |
| 5,358,500 A | 10/1994 | Lavon et al. |
| 5,368,584 A | 11/1994 | Clear et al. |
| 5,368,585 A | 11/1994 | Dokken |
| 5,370,632 A | 12/1994 | Beplate |
| 5,370,634 A | 12/1994 | Ando et al. |
| 5,373,587 A | 12/1994 | Sexton |
| 5,374,262 A | 12/1994 | Keuhn, Jr. et al. |
| 5,383,872 A | 1/1995 | Roessler et al. |
| 5,386,595 A | 2/1995 | Kuen et al. |
| 5,397,639 A | 3/1995 | Tollini |
| 5,399,219 A | 3/1995 | Roessler et al. |
| 5,401,275 A | 3/1995 | Flug et al. |
| 5,409,476 A | 4/1995 | Coates |
| 5,423,789 A | 6/1995 | Kuen |
| 5,445,628 A | 8/1995 | Gipson et al. |
| 5,451,219 A | 9/1995 | Suzuki et al. |
| 5,462,541 A | 10/1995 | Bruemmer et al. |
| 5,489,282 A | 2/1996 | Zehner et al. |
| 5,496,298 A | 3/1996 | Kuepper et al. |
| 5,499,978 A | 3/1996 | Buell et al. |
| 5,500,063 A | 3/1996 | Jessup |
| 5,509,915 A | 4/1996 | Hanson et al. |
| 5,527,302 A | 6/1996 | Endres et al. |
| H1558 H | 7/1996 | Goulait et al. |
| 5,531,731 A | 7/1996 | Brusky |
| 5,531,732 A | 7/1996 | Wood |
| 5,537,722 A | 7/1996 | Niederhofer et al. |
| 5,540,796 A | 7/1996 | Fries |
| 5,545,158 A | 8/1996 | Jessup |
| 5,545,275 A | 8/1996 | Herrin et al. |
| 5,549,592 A | 8/1996 | Fries et al. |
| 5,554,146 A | 9/1996 | Niederhofer et al. |
| 5,562,650 A | 10/1996 | Everett et al. |

| | | |
|---|---|---|
| 5,569,232 A | 10/1996 | Roe et al. |
| 5,569,234 A | 10/1996 | Buell et al. |
| 5,571,586 A | 11/1996 | Gobran |
| 5,575,784 A | 11/1996 | Ames-Ooten et al. |
| 5,582,606 A | 12/1996 | Bruemmer et al. |
| 5,591,152 A | 1/1997 | Buell et al. |
| 5,593,401 A | 1/1997 | Sosalla et al. |
| 5,601,546 A | 2/1997 | Tanji et al. |
| 5,605,735 A | 2/1997 | Zehner et al. |
| 5,607,416 A | 3/1997 | Yamamoto et al. |
| 5,611,789 A | 3/1997 | Seth |
| 5,618,366 A | 4/1997 | Suekane |
| 5,624,420 A | 4/1997 | Bridges et al. |
| 5,624,424 A | 4/1997 | Saisaka et al. |
| 5,624,428 A | 4/1997 | Sauer |
| 5,624,429 A | 4/1997 | Long et al. |
| 5,626,574 A | 5/1997 | Sasaki et al. |
| 5,628,738 A | 5/1997 | Suekane |
| 5,629,063 A | 5/1997 | Gobran |
| 5,634,916 A | 6/1997 | Lavon et al. |
| H1674 H | 8/1997 | Ames et al. |
| 5,656,111 A | 8/1997 | Dilnik et al. |
| 5,662,637 A | 9/1997 | Kitaoka et al. |
| 5,662,638 A | 9/1997 | Johnson et al. |
| 5,665,084 A | 9/1997 | Richmond |
| 5,669,897 A | 9/1997 | Lavon et al. |
| 5,685,873 A | 11/1997 | Bruemmer |
| 5,685,874 A | 11/1997 | Buell et al. |
| 5,690,626 A | 11/1997 | Suzuki et al. |
| 5,690,627 A | 11/1997 | Clear et al. |
| 5,693,038 A | 12/1997 | Suzuki et al. |
| 5,695,488 A | 12/1997 | Sosalla |
| 5,695,868 A | 12/1997 | McCormack |
| D389,320 S | 1/1998 | Vinnage et al. |
| 5,707,364 A | 1/1998 | Coates |
| 5,711,832 A | 1/1998 | Glaug et al. |
| 5,725,518 A | 3/1998 | Coates |
| 5,759,317 A | 6/1998 | Justmann |
| 5,772,649 A | 6/1998 | Siudzinski |
| 5,772,825 A | 6/1998 | Schmitz |
| 5,788,685 A | 8/1998 | Ronnberg et al. |
| 5,788,797 A | 8/1998 | Herrin et al. |
| 5,795,433 A | 8/1998 | Niedermeyer |
| 5,827,259 A | 10/1998 | Laux et al. |
| 5,827,260 A | 10/1998 | Suzuki et al. |
| 5,830,206 A | 11/1998 | Larsson |
| 5,843,056 A | 12/1998 | Good et al. |
| 5,855,574 A | 1/1999 | Kling et al. |
| 5,876,531 A | 3/1999 | Jacobs et al. |
| 5,897,545 A | 4/1999 | Kline et al. |
| 5,899,896 A | 5/1999 | Suprise et al. |
| 5,904,802 A | 5/1999 | Niedermeyer |
| 5,916,203 A | 6/1999 | Brandon et al. |
| 5,916,207 A | 6/1999 | Toyoda et al. |
| 5,919,334 A | 7/1999 | Niedermeyer |
| 5,944,707 A | 8/1999 | Ronn |
| 5,961,761 A | 10/1999 | Heindel et al. |
| 5,971,153 A | 10/1999 | Bauer et al. |
| 6,022,430 A | 2/2000 | Blenke et al. |
| 6,022,431 A | 2/2000 | Blenke et al. |
| 6,022,432 A | 2/2000 | Elsberg et al. |
| 6,030,373 A | 2/2000 | VanGompel et al. |
| 6,036,805 A | 3/2000 | McNichols |
| 6,045,543 A | 4/2000 | Pozniak et al. |
| 6,113,717 A | 9/2000 | Vogt et al. |
| 6,149,638 A | 11/2000 | Vogt et al. |
| 6,287,287 B1 | 9/2001 | Elsberg |
| 6,322,552 B1 | 11/2001 | Blenke et al. |

FOREIGN PATENT DOCUMENTS

| | | |
|---|---|---|
| EP | 0 251 251 A3 | 1/1988 |
| EP | 0 463 276 A1 | 1/1992 |
| EP | 0 532 034 A2 | 3/1993 |
| EP | 0 544 703 B1 | 6/1993 |
| EP | 0 696 911 B1 | 2/1996 |
| EP | 0 753 292 A2 | 1/1997 |
| EP | 0 487 758 B1 | 3/1997 |
| EP | 0 597 331 B1 | 11/1997 |
| EP | 0 809 992 A1 | 12/1997 |
| EP | 0 878 180 A2 | 11/1998 |
| FR | 2566631 | 1/1986 |
| GB | 1 520 740 | 8/1978 |
| GB | 2 244 422 B | 12/1991 |
| GB | 2 267 024 B | 11/1993 |
| GB | 2 288 314 A | 10/1995 |
| GB | 2 288 315 A | 10/1995 |
| GB | 2 288 316 A | 10/1995 |
| GB | 2 291 783 A | 2/1996 |
| GB | 2 294 867 A | 5/1996 |
| GB | 2 297 473 A | 6/1996 |
| GB | 2 308 290 A | 6/1997 |
| JP | 6-77718 U | 11/1994 |
| JP | 7-213553 A | 8/1995 |
| JP | 7-227407 A | 8/1995 |
| JP | 7-255773 A | 10/1995 |
| JP | 7-299094 A | 11/1995 |
| JP | 8-229072 A | 9/1996 |
| JP | 9-287 U | 5/1997 |
| JP | 11-47188 A | 2/1999 |
| WO | WO 83/04163 A1 | 12/1983 |
| WO | WO 90/07313 A1 | 7/1990 |
| WO | WO 91/04724 A1 | 4/1991 |
| WO | WO 91/08725 A1 | 6/1991 |
| WO | WO 92/22274 A1 | 12/1992 |
| WO | WO 93/09742 A1 | 5/1993 |
| WO | WO 94/17768 A1 | 8/1994 |
| WO | WO 95/01148 A1 | 1/1995 |
| WO | WO 95/02383 A1 | 1/1995 |
| WO | WO 95/13772 A1 | 5/1995 |
| WO | WO 95/22951 A1 | 8/1995 |
| WO | WO 95/27460 A1 | 10/1995 |
| WO | WO 95/27462 A1 | 10/1995 |
| WO | WO 95/29657 A1 | 11/1995 |
| WO | WO 96/03101 A1 | 2/1996 |
| WO | WO 96/18315 A1 | 6/1996 |
| WO | WO 96/29037 A1 | 9/1996 |
| WO | WO 96/32084 A1 | 10/1996 |
| WO | WO 97/15260 A1 | 5/1997 |
| WO | WO 97/23186 A1 | 7/1997 |
| WO | WO 97/25951 A1 | 7/1997 |
| WO | WO 97/31605 A1 | 9/1997 |
| WO | WO 97/32555 A1 | 9/1997 |
| WO | WO 97/33547 A1 | 9/1997 |
| WO | WO 97/46197 A1 | 12/1997 |
| WO | WO 97/47265 A1 | 12/1997 |
| WO | WO 97/48357 A1 | 12/1997 |
| WO | WO 98/03140 A1 | 1/1998 |
| WO | WO 98/18421 A1 | 5/1998 |
| WO | WO 98/29251 A1 | 7/1998 |
| WO | WO 98/51252 A1 | 11/1998 |
| WO | WO 98/56328 A1 | 12/1998 |
| WO | WO 99/07319 A1 | 2/1999 |
| WO | WO 99/56688 A1 | 11/1999 |
| WO | WO 99/65438 A1 | 12/1999 |
| WO | WO 99/65442 A1 | 12/1999 |
| WO | WO 00/37010 A1 | 6/2000 |
| WO | WO 01/43682 A1 | 6/2001 |
| WO | WO 01/43683 A1 | 6/2001 |
| WO | WO 01/70155 A1 | 9/2001 |

OTHER PUBLICATIONS

Derwent World Patent Database abstract of JP 95–044941 B2: Description of ZUIKO KK (ZUIK–N), "Simple Solid Diaper for Eliminating Waste of Material by Using Square Shape".

Derwent World Patent Database abstract of JP 9–276334 A: Description of Kao Corp (Kaos), "Disposable Baby Nappy".

Derwent World Patent Database abstract of JP 11–070143 A: Description of TOYO EISAI KK (TOEI–N), "Disposable Diaper For Adults And Children".

Derwent World Patent Database abstract of JP 11–076299 A: Description of UNI–CHARM KK (UNIC–N), "Disposable Diaper".

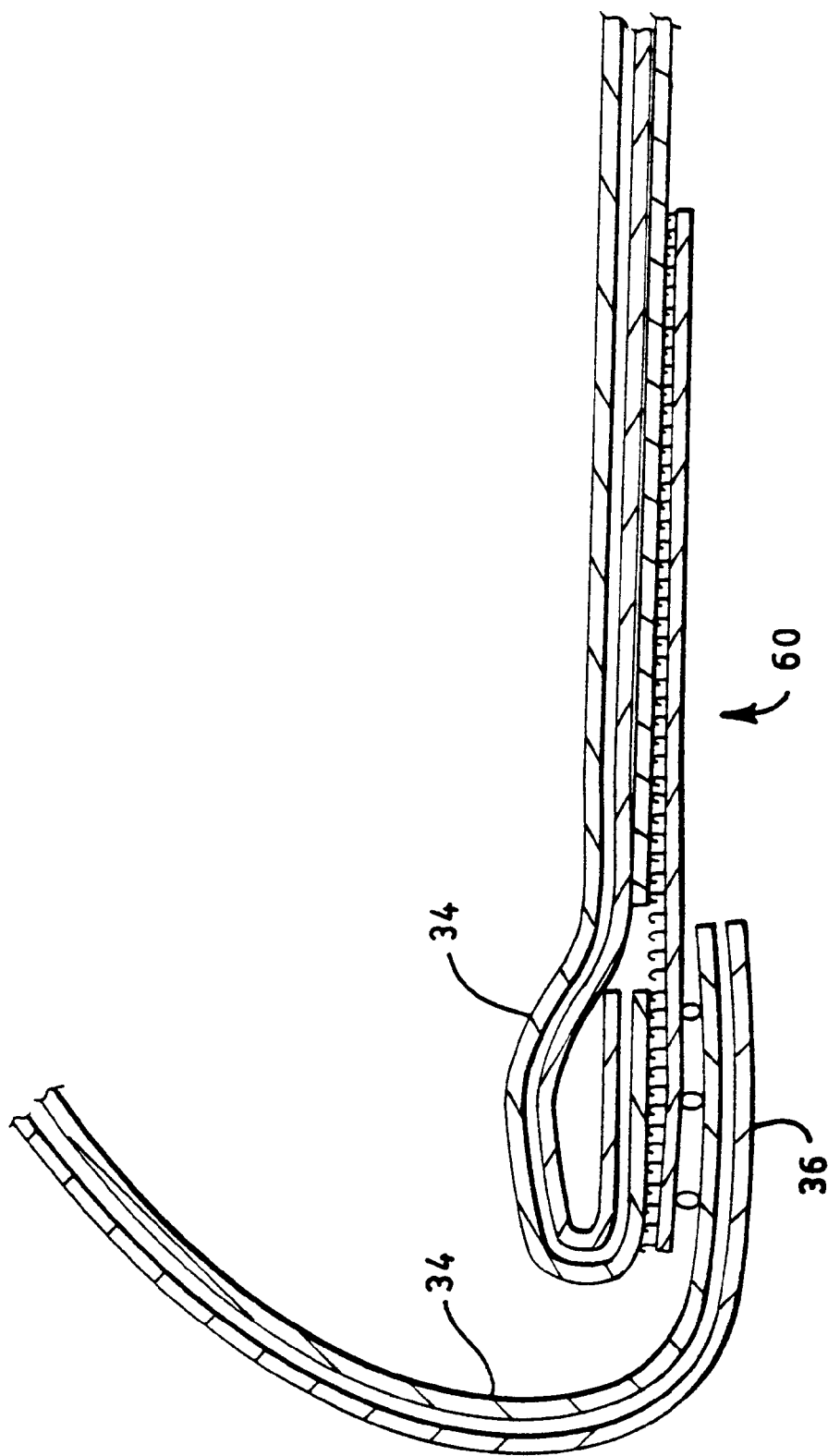

PRE-FASTENED ADJUSTABLE MECHANICAL FASTENER GARMENT

FIELD OF THE INVENTION

The present invention relates to disposable absorbent articles which are adapted to contain body exudates. More particularly, the present invention relates to pant-like disposable absorbent articles having prefastened, refastenable side seams, a waist size adjustment means to maintain the articles about the waist of the wearer, and methods of making the same.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the caregiver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. In such circumstances it is further desirable for the caregiver or the wearer to be able to adjust the fit of the waist area of the article. For example, such absorbent articles can assist in the toilet training of children.

Conventional diapers are not provided in a prefastened condition and have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the exterior surface of the outer cover of the diaper in the front waist portion of the diaper. In such a configuration, the diaper has been positioned between the legs of the wearer while the wearer is lying down and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the caregiver. However, such conventional diapers are not provided in a pant-like, prefastened configuration and, thus, are not configured to be pulled up or down over the hips of the wearer when the fasteners are attached. Moreover, the fasteners on such conventional diapers generally must be disengaged and reattached to further conform the waist portions of the diaper to the wearer. Such disengagement and reattachment for adjustment can be difficult to accomplish when the wearer is active.

Several attempts have been made to provide absorbent articles which effectively contain body exudates, are capable of being pulled up or down over the hips of the wearer and provide ease of cleaning and removal after being soiled. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely, which can undesirably result in leaks. As a result, many of such articles have not contained bodily exudates as effectively as conventional diaper-type articles which can be adjusted to achieve a more conforming fit to the wearer. Moreover, the inspection and removal of soiled absorbent articles which have integral side panels, such as conventional training pants, have not always been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles which can provide the benefits of conventional training pants and conventional diapers. That is, there remains a need for absorbent articles which conform to the wearer to effectively contain bodily exudates, are capable of being pulled up and down over the hips and buttocks of the wearer, are readily secured about and removed from the wearer in a convenient and clean manner, and which allow easy inspection by the care giver to assist in determining whether the article is soiled. Moreover, there is a need for improved methods of reliably and consistently making such pant-like disposable absorbent articles.

SUMMARY OF THE INVENTION

In response to the difficulties and problems discussed above, new prefastened, pant-like disposable absorbent articles that have a waist size adjustment mechanism, and methods of making the same have been discovered. In one aspect, the present invention concerns a pant-like, refastenable, disposable absorbent article which defines an absorbent, a front waist region, a back waist region, a crotch region which extends between and connects the waist regions, a longitudinal direction and a lateral direction. The prefastened absorbent article further defines an exterior surface, an interior surface opposite the exterior surface, a pair of laterally opposed side edges and a pair of longitudinally opposed waist edges. The prefastened absorbent article includes a pair of refastenable side seams and at least one waist size adjustment means. The refastenable side seams refastenably attach the laterally opposed side edges of the front waist region to the back waist region to define a waist opening having a waist perimeter dimension and a pair of leg openings. The waist size adjustment means is for reducing the waist perimeter dimension after the prefastened absorbent article is positioned on the wearer and may be provided by a portion of at least one of the refastenable side seams.

In another aspect, the present invention concerns a pant-like, prefastened, disposable absorbent article which defines an absorbent, a front waist region, a back waist region, a crotch region which extends between and connects the waist regions, a longitudinal direction and a lateral direction. The prefastened absorbent article further defines an exterior surface, an interior surface opposite the exterior surface, a pair of laterally opposed side edges and a pair of longitudinally opposed waist edges. The prefastened absorbent article includes a pair of continuous fasteners permanently attached to the laterally opposed side edges in one of the waist regions. Each of the continuous fasteners includes a first engageable portion and at least one of the continuous fasteners includes a second engageable portion. The first engageable portions are refastenably attached to the opposite waist region of the disposable absorbent article to provide a pair of refastenable side seams. The refastenable side seams join the waist regions to define a waist opening having a waist perimeter dimension and a pair of leg openings, thereby providing the prefastened absorbent article. The second engageable portion of the continuous fastener extends from at least one of the refastenable side seams and is configured to releasably engage the opposite waist region to reduce the waist perimeter dimension and assist in maintaining the prefastened absorbent article about a wearers hips after the prefastened absorbent article is positioned on the wearer.

In yet another aspect, the present invention concerns a pant-like, prefastened, disposable absorbent article which defines an absorbent, a front waist region, a back waist region, a crotch region which extends between and connects the waist regions, a longitudinal direction and a lateral direction. The prefastened absorbent article further defines an exterior surface, an interior surface opposite the exterior surface, a pair of laterally opposed side edges and a pair of longitudinally opposed waist edges. The prefastened absorbent article includes a pair of fasteners which include primary and secondary fasteners. The pair of fasteners is permanently attached to the side edges of the back waist region. The pair of fasteners further includes an inboard longitudinal edge, an outboard longitudinal edge, and an intermediate portion between the primary and the secondary fasteners. The side edges of the front waist region are refastenably attached to the primary fasteners to form a pair of refastenable side seams which define a waist opening having a waist perimeter dimension and a pair of leg openings in the prefastened absorbent article. The secondary fasteners are configured to refastenably attach to the exterior surface of the absorbent article in the front waist region to reduce the waist perimeter dimension after the prefastened absorbent article is positioned on the wearer.

In still another aspect, the present invention concerns a pant-like, prefastened, disposable absorbent article which defines an absorbent chassis, a front waist region, a back waist region, a crotch region which extends between and connects the waist regions, a longitudinal direction, a lateral direction, a pair of opposed side edges and a pair of opposed waist edges. The pant-like, prefastened, disposable absorbent article is made by a process which comprises the steps of:

a) providing a continuous web of interconnected absorbent chassis;
b) permanently attaching a pair of laterally opposed fasteners to the side edges in the back waist region;
c) selectively cutting the continuous web of interconnected absorbent chassis into discrete absorbent articles;
d) folding each of the discrete absorbent articles about a fold line that extends in a lateral direction through the crotch region of the article thereby positioning the front waist region and the back waist region in a facing relationship; and
e) refastenably attaching a first portion of the fasteners in the back waist region to the opposed side edges in the front waist region to create a pair of side seams and to define a waist opening having a waist perimeter dimension and a pair of leg openings. A second portion of each of the fasteners is configured to refastenably attach to an exterior surface of the absorbent article in the front waist region to reduce the waist perimeter dimension after the prefastened absorbent article is positioned on the wearer.

The present invention advantageously provides pant-like, prefastened, disposable absorbent articles which include a waist size adjustment mechanism and methods of making the same. In particular, the present invention provides pant-like, prefastened, disposable absorbent articles which are capable of being reliably pulled up or down over the hips of the wearer to assist in the toilet training of the wearer similar to conventional training pants. Moreover, once the prefastened absorbent article is positioned on the hips of the wearer, the waist perimeter dimension may be reduced by the wearer or the caregiver without disengaging the prefastened side seams. The prefastened absorbent article thereby conforms to the body of the wearer to effectively contain bodily exudates. Additionally, similar to conventional diapers, the prefastened absorbent articles of the present invention can advantageously be applied to and removed from the wearer with relative ease and cleanliness after they have been soiled. Further, the prefastened absorbent articles of the present invention allow easy inspection by the caregiver to assist in determining whether the article is soiled, similar to conventional diapers.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

FIG. 3-A representatively shows a section view of the continuous fastener of the absorbent article of FIG. 3 wherein the interior surface of the back waist region is refastenably engaged to the interior surface of the front waist region to comprise the refastenable side seam;

FIG. 3-B representatively shows a section view of an alternate configuration of the continuous fastener of the absorbent article of FIG. 3 wherein the exterior surface of the back waist region is refastenably engaged to the interior surface of the front waist region to comprise the refastenable side seam;

FIG. 3-C representatively shows a section view of an alternate configuration of the continuous fastener of the absorbent article of FIG. 3 wherein the exterior surface of the back waist region is refastenably engaged to the exterior surface of the front waist region to comprise the refastenable side seam;

FIG. 4-A representatively shows a section view of the prefastened absorbent article of FIG. 4 along line A—A;

FIG. 4-B representatively shows a section view of the prefastened absorbent article of FIG. 4 along line B—B;

FIG. 5-B representatively shows a front plan view of an alternate configuration of the fastener of the absorbent article of FIG. 3, with portions of the article partially cut away to show underlying features;

FIG. 6-A representatively shows a section view of the fastener of the absorbent article of FIG. 6;

FIG. 6-B representatively shows a section view of an alternate configuration of the fastener of FIG. 6; and FIG. 6-C representatively shows a section view of an alternate configuration of the fastener of FIG. 6.

DETAILED DESCRIPTION OF THE INVENTION

The present invention concerns pant-like, prefastened, disposable absorbent articles which are adapted to be worn adjacent to the body of a wearer to absorb and contain various exudates discharged from the body, and methods of making the same. The prefastened absorbent articles are configured to closely conform to the body of the wearer to effectively contain body exudates while remaining capable of being pulled up or down over the hips and buttocks of the wearer. The prefastened absorbent articles are also refastenable such that they can be secured to and removed directly from the waist of the wearer and easily inspected to determine if they have been soiled during use. As such, the pant-like, prefastened, disposable absorbent articles of the present invention can function in a similar manner to conventional training pants when left in the prefastened, pant-like configuration, or they can be unfastened prior to or during use to function in a refastenable manner similar to conventional diapers. Moreover, the prefastened absorbent articles include a waist size adjustment means allowing the wearer or the caregiver to further improve the fit of the article once it is positioned on the hips of the wearer without disengaging the prefastened side seams. As used herein, the term "disposable" refers to articles which are intended to be discarded after a limited use and which are not intended to be laundered or otherwise restored for reuse.

The pant-like, prefastened disposable absorbent articles of the present invention will be described in terms of a disposable, pant-like diaper article which is adapted to be worn by infants about the lower torso. In particular, the pant-like disposable absorbent articles will be described in terms of a pant-like, prefastened, disposable diaper having a waist size adjustment means. It is understood that the articles and methods of the present invention are equally adaptable for other types of absorbent articles such as adult incontinent products, training pants, feminine hygiene products, other personal care or health care garments, and the like.

Figure 1:
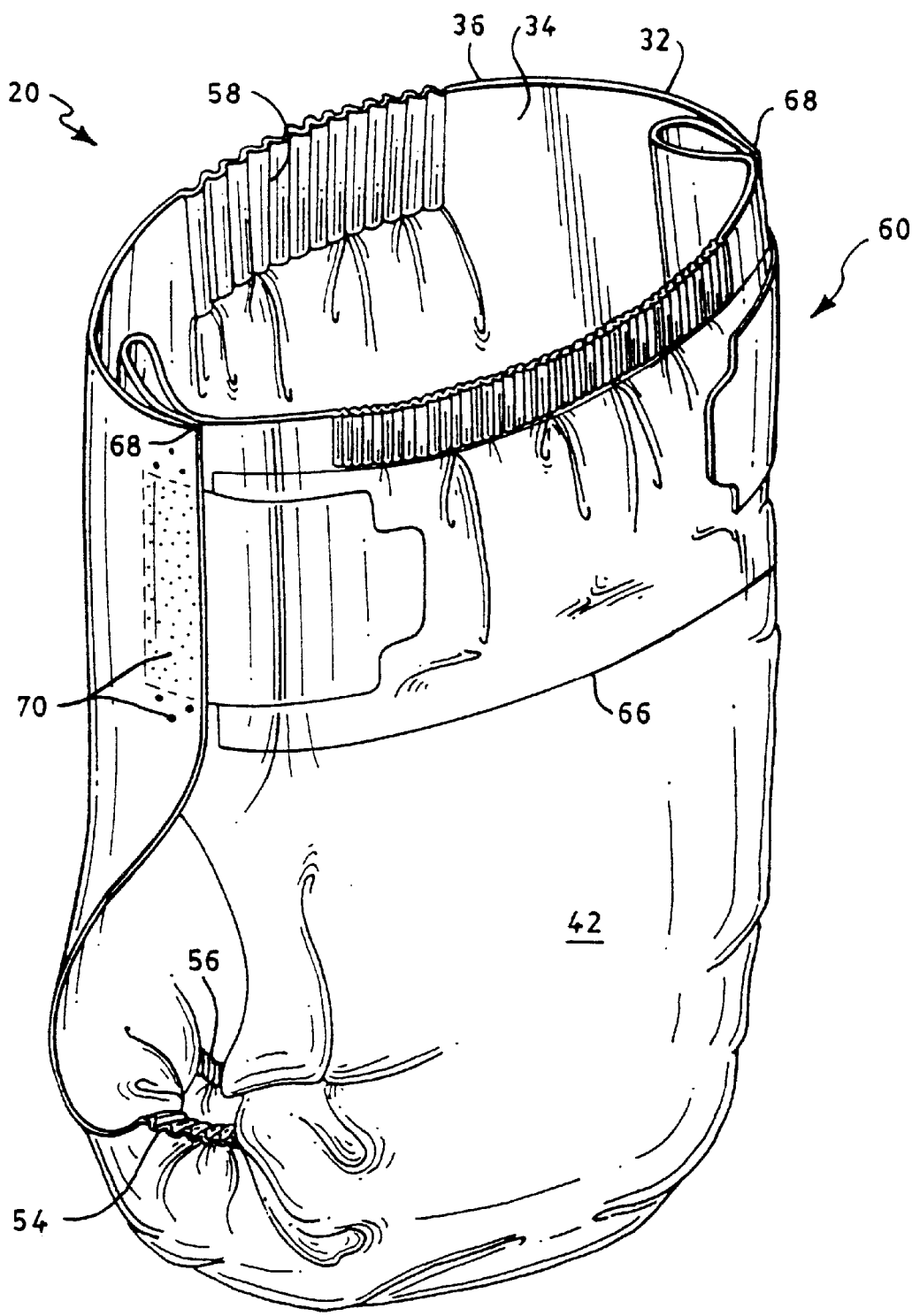
FIG. 1 representatively shows a perspective view of an example of a prefastened absorbent article of the present invention.
Figure 2:
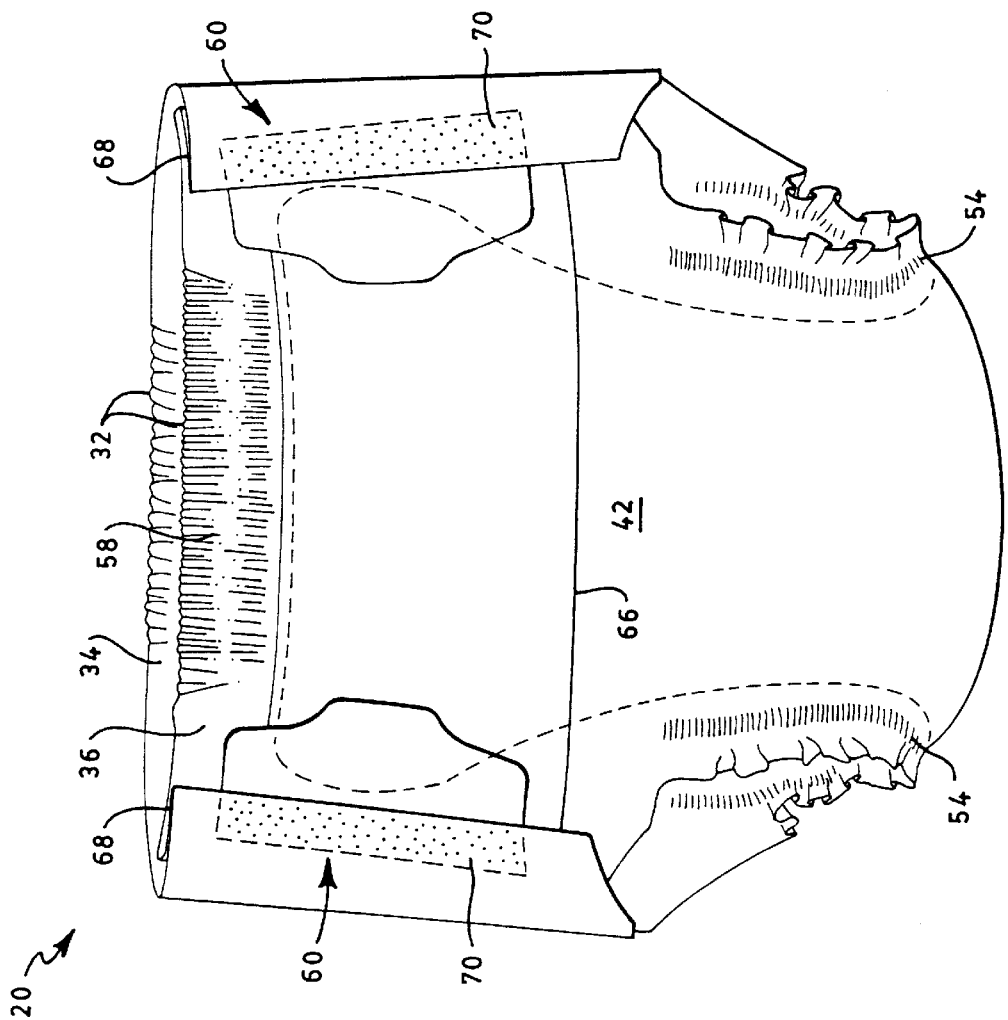
FIG. 2 representatively shows a front plan view of the prefastened absorbent article of FIG. 1.
Figure 3:
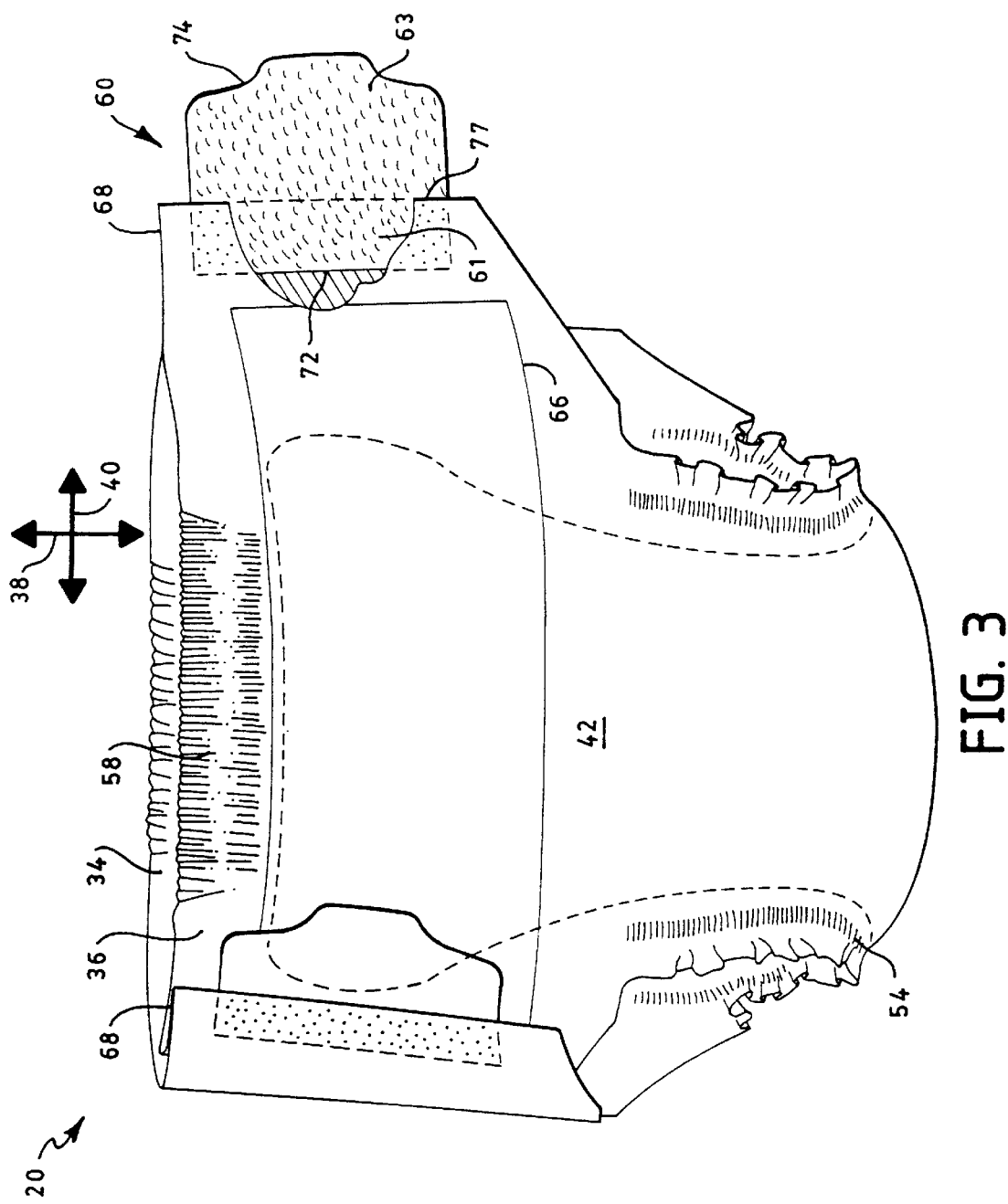
FIG. 3 representatively shows a front plan view of the prefastened absorbent article of FIG. 1 with one of the waist size adjustment means of the continuous fastener in the unengaged position, with portions of the article partially cut away to show the underlying features.
Figure 4:
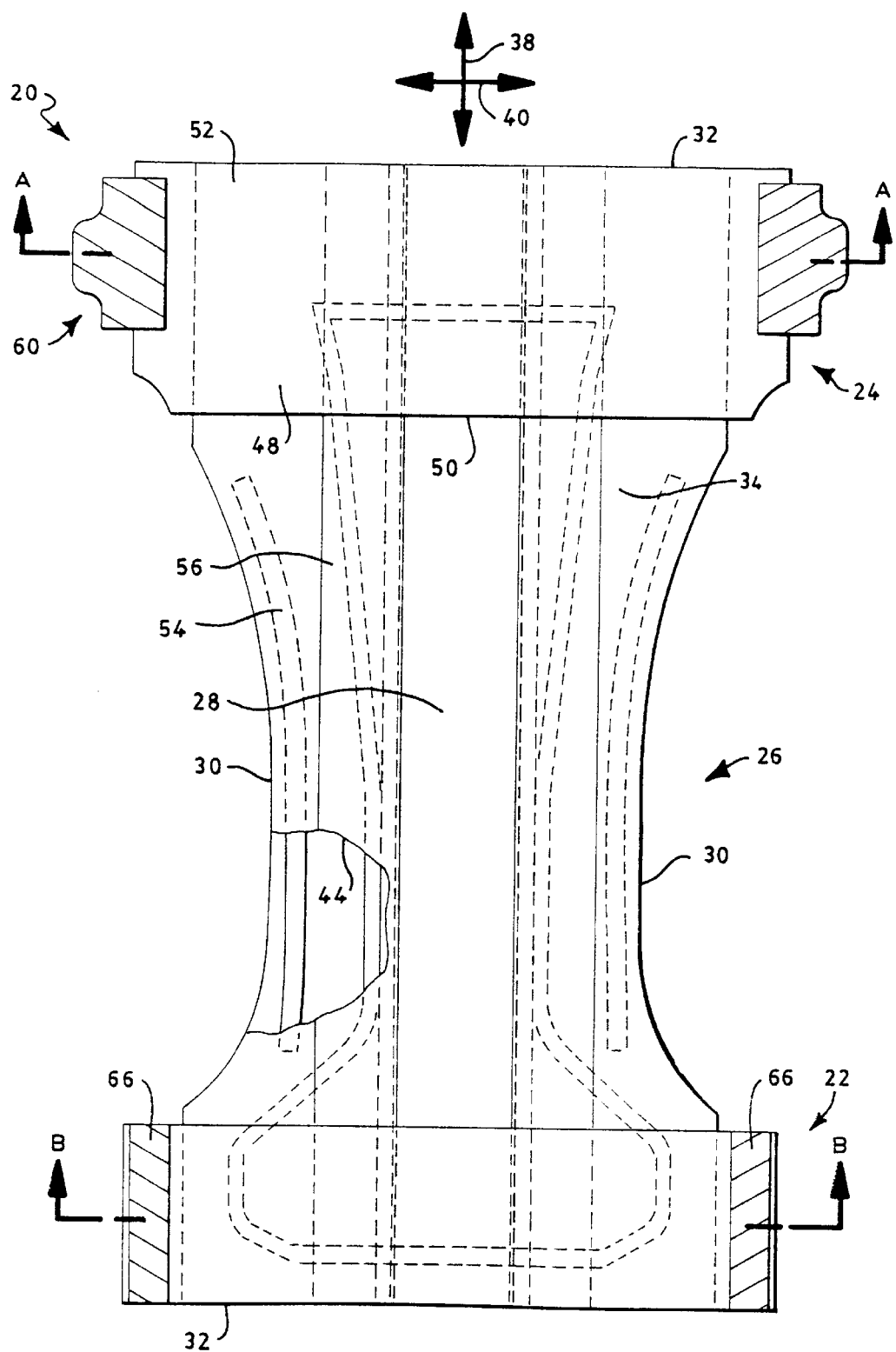
FIG. 4 representatively shows a plan view of the prefastened absorbent article of FIG. 1 in an unfastened, stretched and laid flat condition with the surface of the article which contacts the wearer's skin facing the viewer and with portions of the article partially cut away to show the underlying features.
Figure 4A:
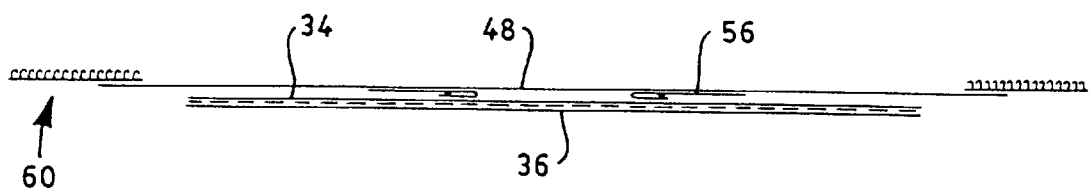
Figure 4B:
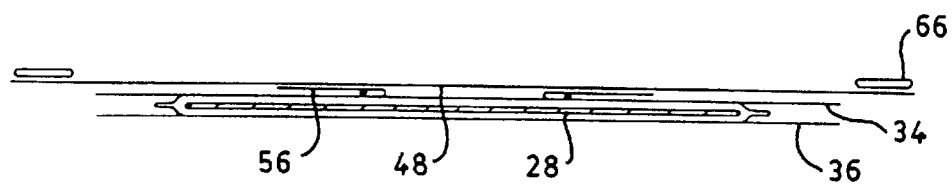

FIG. 1 representatively illustrates an example of a prefastened pant-like, refastenable disposable diaper, as generally indicated at 20, of the present invention. FIG. 2 representatively illustrates a front plan view of the prefastened diaper of FIG. 1. FIG. 3 representatively illustrates a front plan view of the diaper in FIG. 1 wherein one of the continuous fasteners is disengaged and portions of the diaper are partially cut away to show the underlying features. FIG. 4 representatively illustrates the prefastened diaper of FIG. 1 in an unfastened, stretched and laid flat configuration with the surface of the diaper adapted to contact the wearer's skin facing the viewer and with portions of the diaper partially cut away to show the underlying features. As illustrated in FIG. 4, the diaper 20 defines an absorbent 28, a front waist region 22, a back waist region 24, a crotch region 26 which extends between and connects the front and back waist regions 22 and 24, a longitudinal direction 38 and a lateral direction 40. The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer.

The diaper 20 defines a pair of laterally opposed side edges 30, a pair of longitudinally opposed waist edges 32, an interior surface 34 which is configured to contact the wearer, and an exterior surface 36 opposite the interior surface 34 which is configured to contact the wearer's clothing in use. The illustrated diaper 20 also includes an outer cover 42 and a bodyside liner 44 which is connected to the outer cover 42 in a superposed relation. An absorbent 28 is located between the outer cover 42 and the bodyside liner 44. The laterally opposed side edges 30 of the diaper 20 are generally defined by the side edges of the outer cover 42 which further define leg openings which may be curvilinear. The waist edges 32 of the diaper 20 are generally defined by the waist edges of the outer cover 42 and define a waist opening which is configured to encircle the waist of the wearer when worn. The absorbent 28 is configured to contain and/or absorb any body exudates discharged from the wearer. The diaper 20 may further include leg elastics 54, containment flaps 56 and waist elastics 58 as are known to those skilled in the art. It should be recognized that individual components of the diaper 20 may be optional depending upon the intended use of the diaper 20.

The diaper 20 further includes refastenable, prefastened fasteners 60. The fasteners 60 releasably engage the opposed side edges 30 of the diaper 20 in the opposite waist regions to form refastenable side seams 68. In addition, at least one waist size adjustment means for reducing the waist perimeter dimension of the waist opening about the wearer is provided by a portion of at least one of the fasteners that provide the refastenable side seams 68. The refastenable side seams 68 may also include passive bonds 70 incorporated within the side seams 68 which assist the continuous fasteners 60 in releasably securing the front waist region 22 to the back waist region 24. Further, the fastening system 60 may include an attachment panel 66 located on the front or back waist region 22 and 24, opposite the fasteners 60 to which the first engageable portion of the continuous fasteners 60 are releasably engaged to form the prefastened, refastenable side seams 68.

The diaper 20 may be of various suitable shapes. For example, in the unfastened configuration as illustrated in FIG. 4, the diaper may have an overall rectangular shape, T-shape or an approximately hourglass shape. In the shown embodiment, the diaper 20 has a generally I-shape in an unfastened configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the absorbent 28 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent 28 may be connected to the outer cover 42 using conventional fasteners such as buttons, hook and loop type fasteners, adhesive tape fasteners, and the like. The other components of the diaper 20 may be suitably connected together using similar means. Similarly, other diaper components, such as the elastic members 54 and 58 and the fasteners 60, may be assembled into the diaper 20 article by employing the above-identified attachment mechanisms. Desirably, the majority of the diaper components are assembled together using ultrasonic bonding techniques for reduced manufacturing cost.

The outer cover 42 of the diaper 20, as representatively illustrated in FIGS. 1–4, may suitably be composed of a material which is either liquid permeable or liquid impermeable. It is generally preferred that the outer cover 42 be formed from a material which is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). If it is desired to present the outer cover 42 with a more clothlike feeling, the outer cover 42 may comprise a polyolefin film having a nonwoven web laminated to the exterior surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers. The polypropylene fibers have a thickness of about 1.5 to 2.5 denier per filament, which nonwoven web has a basis weight of about 17 grams per square meter (0.5 ounce per square yard). The outer cover 42 may otherwise include bicomponent fibers such as polyethylene/polypropylene bicomponent fibers. Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent 28. Still further, the outer cover 42 may optionally be composed of a micro-porous "breathable" material which permits vapors to escape from the absorbent 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued to McCormack et al. and U.S. Pat. No. 5,843,056 issued Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference. The outer cover 42 can also be embossed or otherwise provided with a matte finish to provide a more aesthetically pleasing appearance.

The bodyside liner 44, as representatively illustrated in FIG. 4, suitably presents a bodyfacing surface which is compliant, soft feeling, and nonirritating to the wearer's skin. Further, the bodyside liner 44 may be less hydrophilic than the absorbent 28, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent 28.

Various woven and nonwoven fabrics can be used for the bodyside liner 44. For example, the bodyside liner may be composed of a meltblown or spunbonded web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In a particular embodiment of the present invention, the bodyside liner 44 comprises a nonwoven, spunbond, polypropylene fabric composed of about 2.8–3.2 denier fibers formed into a web having a basis weight of about 20 grams per square meter and a density of about 0.13 grams per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto which is configured to be transferred to the wearer's skin.

The absorbent 28 of the diaper 20, as representatively illustrated in FIG. 4, may suitably comprise a matrix of hydrophilic fibers, such as a web of cellulosic fluff, mixed with particles of a high-absorbency material commonly known as superabsorbent material. In a particular embodiment, the absorbent 28 comprises a matrix of cellulosic fluff such as wood pulp fluff and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent 28 to better contain and absorb body exudates. The concentration of the superabsorbent particles may also vary through the thickness of the absorbent 28. Alternatively, the absorbent 28 may comprise a laminate of fibrous webs and superabsorbent material or other suitable means of maintaining a superabsorbent material in a localized area.

The absorbent 28 may have any of a number of shapes. For example, the absorbent may be rectangular, I-shaped, or T-shaped. It is generally preferred that the absorbent 28 be narrow in the crotch region 26 of the diaper 20. It has been found that the absorbent 28 of the present invention is particularly useful when the width dimension in the crotch region 26 is from about 2.5 to about 12.7 centimeters (1.0 to about 5.0 inches), desirably no more than about 7.6 centimeters (3.0 inches) and more desirably no more than about 5.1 centimeters (2.0 inches). The narrow crotch width dimension of the absorbent 28 allows the absorbent 28 to better fit between the legs of the wearer. The size and the absorbent capacity of the absorbent 28 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent 28.

Optionally, a substantially hydrophilic tissue wrapsheet may be employed to help maintain the integrity of the airlaid fibrous structure of the absorbent 28. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. The wrapsheet material on one side of the absorbent fibrous mass may be bonded to the wrapsheet located on the opposite side of the fibrous mass to effectively entrap the absorbent 28.

As representatively illustrated in FIGS. 1 and 4, the disposable diaper 20 may include a pair of containment flaps 56 which are configured to provide a barrier to the lateral flow of body exudates. The containment flaps 56 may be located along the laterally opposed side edges 30 of the diaper adjacent the side edges of the absorbent 28. Each containment flap 56 typically defines an unattached edge which is configured to maintain an upright, perpendicular configuration in at least the crotch region 26 of the diaper 20 to form a seal against the wearer's body. The containment flaps 56 may extend longitudinally along the entire length of the absorbent 28 or may only extend partially along the length of the absorbent 28. When the containment flaps 56 are shorter in length than the absorbent 28, the containment flaps 56 can be selectively positioned anywhere along the side edges 30 of diaper 20 in the crotch region 26. In a particular aspect of the invention, the containment flaps 56 extend along the entire length of the absorbent 28 to better contain the body exudates.

Such containment flaps 56 are generally well known to those skilled in the art. For example, suitable constructions and arrangements for containment flaps 56 are described in U.S. Pat. No. 4,704,96 issued Nov. 3, 1987, to K. Enloe, the disclosure of which is hereby incorporated by reference.

The diaper 20 of the different aspects of the present invention may further include elastics at the waist edges 32 and side edges 30 of the diaper 20 to further prevent leakage of body exudates and support the absorbent 28. For example, as representatively illustrated in FIGS. 1–4, the diaper 20 of the present invention may include a pair of leg elastic members 54 which are connected to the laterally opposed side edges 30 of the diaper 20 in the crotch region 26. The diaper 20 may also include a pair of waist elastic members 58 which are connected to the longitudinally opposed waist edges 32 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics may also include such materials as polyurethane, synthetic and natural rubber.

The diaper 20 of the different aspects of the present invention may further include a fit panel 48 superimposed adjacent to the waist edge 30 in at least one of the waist sections 22 and 24, to provide a more comfortable, contouring fit about the wearer. For example, as illustrated in FIG. 4, the diaper 20 may include a fit panel 48 superimposed adjacent the waist edge 30 on either the interior or exterior surface 34 and 36 of the diaper 20. Or there may be a fit panel located on both surfaces 34 and 36 of the diaper 20 simultaneously. The diaper may include a fit panel disposed in both waist sections 22 and 24 and desirably the diaper includes a fit panel in at least the rear waist section 24. Desirably, the fit panel is extensible or elastomeric. For example, as representatively illustrated in FIG. 4, the diaper 20 includes an elastomeric fit panel 48 on the interior surface 34 of the diaper 20 which is configured to elongate in the lateral direction 40 to provide an improved fit and appearance of the absorbent article about the wearer. This is accomplished by providing a means for the waist region to expand, thereby increasing the waist perimeter dimension to assist in applying the diaper 20 on the wearer. Desirably the elastomeric or extensible fit panel allows the waist perimeter dimension to expand at least about 20 percent, more desirably at least about 40 percent and even more desirably at least about 50 percent. The fit panel is further capable of initially providing a conforming fit about the wearer and maintaining such fit throughout the use of such article. The fit panel is also configured such that the absorbent 28 has the ability to expand, contract and receive body exudates without adversely affecting the positioning of the fit panel and the article about the waist of the wearer. Thus, with such a fit panel, movements of the wearer may move the absorbent but do not adversely affect the overall positioning and fit of the article on the wearer. Such improved fit can result in reduced leakage from the absorbent article and a more aesthetically pleasing appearance.

As representatively illustrated in FIG. 4, when the fit panel 48 is located on the interior surface 34 it may also extend beyond the side edges of the absorbent 28 of the diaper 20 and be generally coterminous with the waist edge 32 of the diaper 20 in the respective waist section 22 or 24. When located on the interior surface 34 of the diaper 20, the fit panel 48 may define a free edge 50 which extends longitudinally inward towards the crotch region 26 of the diaper 20. In a particular embodiment the free edge 50 of the fit panel 48 is configured to remain at least partially unattached to the bodyside liner 44 of the diaper 20 when in use to allow the absorbent 28 to move and expand to receive and contain body exudates. The unattached free edge 50 may also form a pocket between the fit panel 48 and the bodyside liner 44 which is configured to further contain body exudates. The free edge 50 of the fit panel 48 may be linear or curvilinear, such as concave, to better fit the wearer. The waist edge 52 of the fit panel 48 may also be curvilinear to better fit the wearer. Desirably, if the free edge 50 is curvilinear, the waist edge 52 is also curvilinear such that consecutive fit panels 48 for multiple articles nest within each other and can be provided from a continuous sheet of material. In such a configuration, the free edge 50 of the first fit panel corresponds to the waist edge 52 of the next fit panel to improve manufacturing and reduce waste.

The fit panel 48 as representatively illustrated in FIG. 4 can be provided in any suitable manner which provides the desired fit properties and performance. Desirably, the fit panel 48 is an elastomeric or extensible material. The materials may include a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220, issued May 5, 1987 to T. Wisneski et al., the disclosure of which has previously been incorporated by reference. Examples of composite fabrics comprising at least one layer of a nonwoven material secured to a fibrous elastic layer are described in European Patent Application NO. EP 0 90 010 published on Apr. 8, 1987 with the inventors listed as J. Taylor et al., the disclosure of which has previously been incorporated by reference. Examples of NBL materials are described in U.S. Pat. No. 5,226,992 issued Jul. 13, 1993 to Mormon, the disclosure of which has previously been incorporated by reference.

Alternatively, the fit panel 48 may be provided by a substantially non-elastomeric material, such as polymer films, woven fabrics, non-woven fabrics, or the like such as described above as being suitable for the outer cover 42 or the bodyside liner 44. For example, the fit panel 48 may include a polyethylene film having a nonwoven web laminated to the outer surface thereof. The fit panel 48 may also be formed of a woven or nonwoven fibrous web layer which has been totally or partially constructed or treated to impart a desired level of liquid impermeability, or wettability and hydrophilicity. Still further, the fit panel 48 may optionally be composed of a micro-porous "breathable" material which permits vapors to escape from between the fit panel 48 and the bodyside liner 44 of the diaper 20.

The fit panel 48 of the different embodiments of the present invention may be attached to the diaper 20 in any suitable manner which provides the desired properties. For example, the fit panel 48 may be attached to the diaper using adhesive, ultrasonic, thermal bonding techniques and the like or combinations thereof. Absorbent articles including such a fit panel 48 and methods of making the same are further described in PCT Patent Application WO 97/48357 published Dec. 24, 1997 and entitled "ABSORBENT ARTICLE HAVING FIT PANEL", the disclosure of which is hereby incorporated by reference.

The diaper 20 of the different aspects of the present invention further includes a pair of refastenable fasteners 60 which provides a pair of prefastened, refastenable side seams 68 and a waist size adjustment means for reducing or increasing the waist perimeter dimension after the diaper has been pulled on over the hips of the wearer. In such a configuration, the prefastened diaper 20 can be pulled on or off over the legs and hips of the wearer. If the prefastened diaper 20 becomes soiled during use, the prefastened, refastenable side seams 68 can be disengaged to easily remove the diaper 20 from the waist of the wearer with reduced risk of undesirably soiling the clothes or legs of the wearer. The prefastened, refastenable side seams 68 can also be easily disengaged to inspect the diaper 20 for possible soiling or to first apply the diaper to the wearer if desired. Thus, the diaper 20 is configured to be pulled on or off over the hips of the wearer similar to conventional training pants and can be readily applied or removed by disengaging the prefastened refastenable side seams 68 similar to conventional diaper articles.

In the illustrated embodiments, the fasteners 60 are permanently attached directly to the side edges 30 of the diaper 20 in one of the waist regions 22 and 24. The fasteners 60 may be permanently adhered to the side edges 30 of the diaper 20 by any means known to those skilled in the art such as adhesive bonds, sonic bonds or thermal bonds.

Desirably, the fasteners 60 are permanently attached to the back waist region 24 in which there is an extensible fit panel 48. Alternatively, the fasteners 60 may be permanently attached to the extensible fit panel 48. Attaching the fasteners 60 onto the same waist region 22 and 24 as the extensible fit panel 48, or directly to the extensible fit panel 48, provides added fit, flexibility, and an optimum seal in the waist regions 22 and 24 once the diaper 20 is positioned on the wearer.

As representatively illustrated in FIG. 3, at least one of the fasteners 60 of the present invention may include a unitary, continuous fastening segment having a first engageable portion 61 which provides the prefastened refastenable side seam 68 and a second engageable portion 63 which provides the waist size adjustment means. When the first engageable portion 61 of the fastener 60 is refastenably engaged, providing the prefastened refastenable side seams 68, the laterally opposed side edges 30 of the diaper 20 define leg openings which are configured to encircle the legs of the wearer. Furthermore, the waist edges 32 of the diaper 20 define a waist opening, having a waist perimeter dimension, which is configured to encircle the waist of the wearer. The use of fasteners which provide both the side seam 68 and a waist size adjustment means with one continuous fastening segment advantageously simplifies the manufacturing process and reduces raw material requirements, resulting in reduced manufacturing costs.

As representatively illustrated in FIG. 4, the disposable diaper 20 of the present invention may include two separate attachment panels 66 located along the opposed side edges 30 on the interior surface 34 of the diaper 20 in the front waist region 22. The first engageable portions 61 of the fastener 60 which are permanently attached to the diaper 20 in the opposed waist region, are releasably engaged to the attachment panels 66 to provide the prefastened refastenable side seams 68. Alternatively, if the fasteners 60 are located on the front waist region 22, the attachment panels 66 may be located along the interior surface 34 of the diaper 20 in the back waist region 24. The attachment panels 66 may be otherwise located on the exterior surface 36 of the diaper of either the front or back waist region 22 and 24 depending upon the location of the fasteners 60. In such configurations the prefastened refastenable side seams 68 may be formed as described above, provided that the surface 34 or 36 of the diaper 20 to which the attachment panels 66 are attached, are configured to be exposed to the first engageable portions 61 of the fastener 60.

Figure 3B:
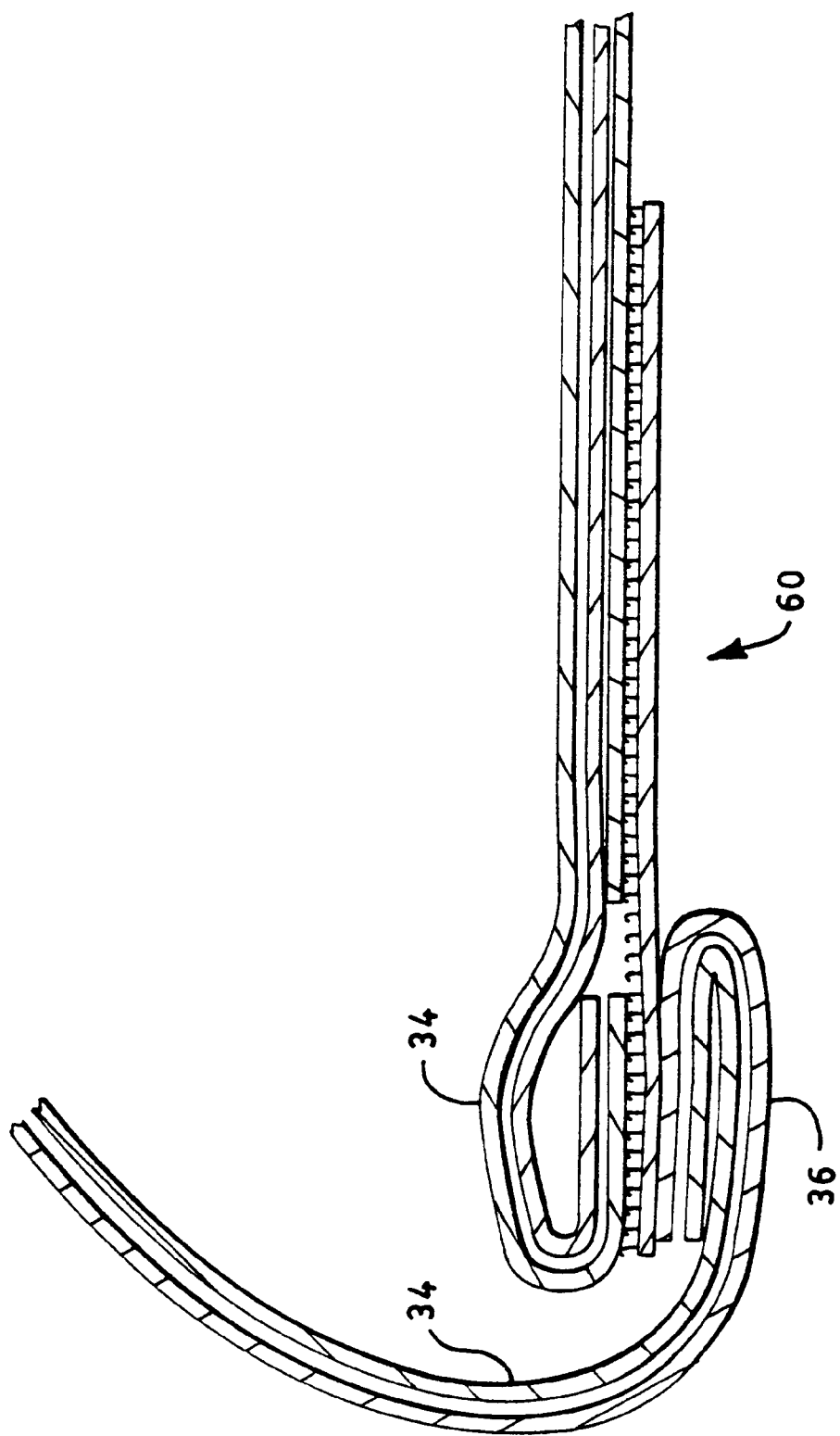
Figure 3C:
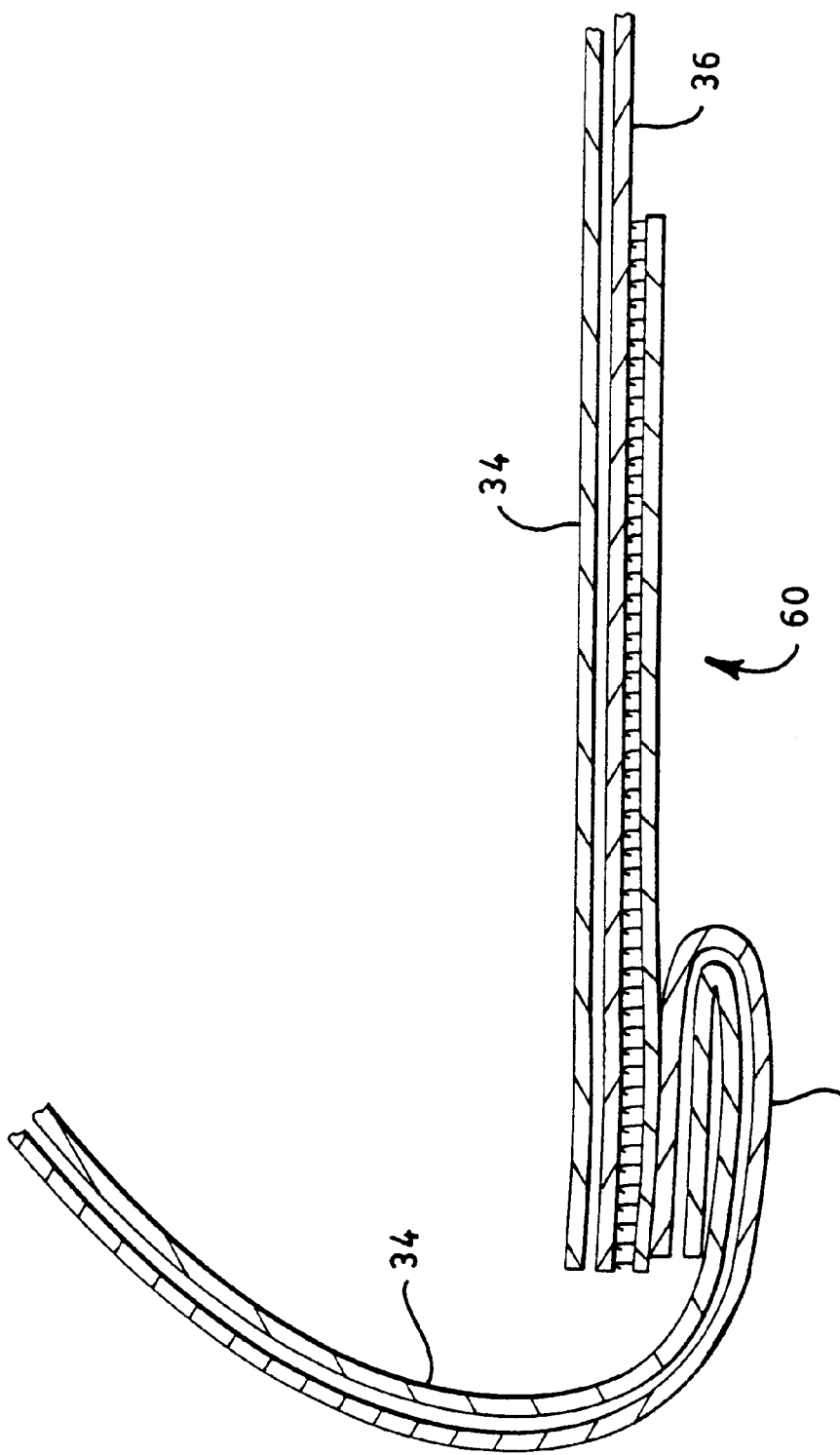

As set forth above, the prefastened refastenable side seams 68 may be arranged in a number of different configurations. Several suitable configurations are representatively illustrated in FIGS. 3A–3C. For example, as representatively illustrated in FIG. 3-A, the prefastened, refastenable side seam 68 of the diaper 20 may be suitably configured such that the interior surface 34 of one waist region 22 and 24 is refastenably attached to the interior surface of the opposite waist region 22 and 24. This arrangement may be accomplished by folding the side edges 30 of the diaper in one waist region 22 or 24 over the exterior surface 36 of the diaper 20 to expose the interior surface 34 of the diaper 20 to the first portion 61 of the fastener 60. This particular configuration has the advantage of creating a seam that is subjected primarily to shear forces in use, providing added strength to the seam.

Alternatively, as representatively illustrated in FIG. 3-B, the prefastened, refastenable side seam 68 of the diaper 20 may be suitably configured such that the interior surface 34 of the diaper in one waist region 22 or 24 is refastenably attached to the exterior surface 36 in the opposite waist region. This configuration may be accomplished by folding the side edges 30 of the diaper in one waist region 22 or 24 over the exterior surface 36 of the diaper 20 to expose the interior surface 34 of the diaper 20 to the first portion 61 of the fastener 60. The exterior surface 36 of the opposite waist region 22 or 24, may simultaneously be exposed by folding over the exterior surface 36 of the diaper 20 to which the fastener 60 is permanently attached. This particular configuration has the advantage of having neither the side seams 68 nor the fasteners 60 exposed to the wearer's skin, thereby reducing the amount of red marking and irritation to the skin of the wearer. Further, this configuration has the added advantage of creating a seam that is subjected primarily to shear forces in use, providing added strength to the seam.

In yet another alternative, the prefastened refastenable side seam 68 of the diaper 20 may be suitably configured such that the exterior surface 36 of one waist region 22 or 24 is refastenably attached to the exterior surface 36 of the opposite waist region. As representatively illustrated in FIG. 3-C, this configuration may be accomplished by folding the side edges 30 of the diaper in one waist region 22 or 24 over to expose the exterior surface 36 of the diaper 20, and permanently attaching the first portion 61 of the fastener 60 to this exposed exterior surface 36. This particular configuration has the advantage of providing a seam which contains less material and is more flexible, thereby reducing discomfort to the wearer.

Desirably, the side seams 68 are configured such that the exterior surface 36 of the front waist region 22 is refastenably attached to the interior surface 34 of the back waist region 24. As such, multiple benefits are realized. For example, the longitudinally inward folded portion of the front waist region 22 ensures that none of the side seam 68 and fastener 60 is exposed to the wearer's skin, reducing undesirable skin irritation. Moreover, in such a configuration, the fastener 60 is subjected to shear forces in use, such that the diaper 20 is more securely fastened upon the wearer. Finally, the fasteners 60, permanently attached to the back waist region 24 of the diaper 20, refastenably engage the diaper 20 in the front waist region 22 increasing the ease with which the wearer or the caregiver can adjust the fit of the diaper 20.

The prefastened, refastenable side seams 68 on the pant-like, disposable absorbent article of the present invention may further include passive bonds 70 for improved reliability of maintaining the article in the prefastened condition, particularly when it is being pulled on or off over the hips of the wearer. Absorbent articles including such passive bonds and methods of making them are further described in U.S. Patent Application entitled "DISPOSABLE ABSORBENT ARTICLES HAVING PASSIVE SIDE BONDS AND ADJUSTABLE FASTENING SYSTEMS" filed in the name of Elsberg on Jun. 19, 1998 and assigned U.S. Ser. No. 09/100,574, and U.S. Patent Application entitled "METHOD OF MAKING AN ABSORBENT ARTICLE WITH PREFASTENED SIDE PANELS AND ABSORBENT ARTICLES MADE BY THE SAME" filed in the name of McNichols on Jun. 19, 1998 and assigned U.S. Ser. No. 09/100,825, the disclosures of which are hereby incorporated by reference.

For example, as representatively illustrated in FIGS. 1–2, the side seams 68 of the diaper 20 may include passive bonds 70 which releasably connect the side edges of the back waist region 24 to the front waist region 22 of the diaper 20. In such a configuration, the passive bonds 70 assist the first engageable portion 61 of the fasteners 60, which provide the refastenable side seams 68, in maintaining the diaper 20 in a prefastened condition as the diaper 20 is pulled up or down over the hips of the wearer. Moreover, the passive bonds 70 assist in securing the refastenable side seams 68 which prevents movement and shifting of the side edges 30 of the waist regions 22 and 24 relative to each other for improved fit and performance. The passive bonds 70 also provide improved hip coverage and prevent rollover or folding of the side edges 30 and waist edges 32 of the prefastened diaper 20 as it is pulled over the wearers hips. Such prevention of rollovers and foldovers can reduce the level of contact between the fasteners 60 and the skin of the wearer, which can desirably result in reduced skin irritation and redness.

The passive bonds 70 may be located on the diaper 20 in any manner which provides the desired improved fastening. For example, as representatively illustrated in FIGS. 1 and 2, the passive bonds 70 may be located laterally inward of the outermost edges 30 of the waist regions 22 and 24, adjacent to or included with the refastenable side seams 68. In such a configuration, the passive bonds 70 connect the front waist region 22 to the back waist region 24 of the diaper 20 in a facing relationship. The passive bonds 70 can be provided by any type of bonding such as thermal, adhesive and ultrasonic bonding as are well known to those skilled in the art and may be discrete point bonds, dashed lines, continuous lines, discontinuous lines and the like or combinations thereof. Alternatively, in one embodiment the passive bonds may be provided by conventional fastener materials such as those described herein as being suitable for the fasteners 62. Moreover, the passive bonds 70 may have any shape such as circular, square, triangular and the like. Desirably, the passive bonds 70 are ultrasonic point bonds for improved manufacturing efficiency. In such a configuration, the ultrasonic passive bonds 70 will be destroyed upon the first opening of the pant-like prefastened diaper 20.

At least one of the continuous fasteners 60 on the disposable diaper 20 of the present invention further includes a waist size adjustment means which provides improved fit and securement of the diaper 20 about the waist of the wearer after the diaper 20 has been placed on the wearer in the prefastened state. The waist size adjustment means of the present invention is configured to reduce the waist perimeter dimension of the waist opening to further conform the waist of the diaper 20 to the waist of the wearer after it has been placed on the wearer. As representatively illustrated in FIG. 3, the waist size adjustment means may be provided by the second engageable portion 63 of the continuous fastener 60. The second engageable portion 63 of the continuous fastener 60 extends from the prefastened, refastenable side seam 68 and is desirably configured to refastenably engage the exterior surface 36 of the front waist region 22 of the diaper 20. Alternatively, the second engageable portion of the continuous fastener 60 may be configured to refastenably engage the exterior surface 36 of the back waist region 24 of the diaper 20. As such, the waist size adjustment means, provided by the second portion 63 of the fastener 60, can encircle the hips of the wearer and reduce the waist perimeter dimension of the waist opening after the diaper is positioned on the wearer.

Desirably, the waist size adjustment means may be refastenably engaged directly with the exterior surface of the outer cover 42 of the diaper 20 to provide improved fit and ease of fastening. Alternatively, an attachment panel 66 may be located on the outer cover 42 to which the waist size adjustment means are releasably engaged. As representatively illustrated in FIG. 1, the disposable diaper 20 of the present invention may include an attachment panel 66 located on the outer cover 42 in one of the waist regions 22 and 24 on the exterior surface 36 of the diaper 20. In such a configuration, the waist size adjustment means, i.e. the second engageable portion 63 in the illustrated embodiments, is refastenably engaged with the attachment panel 66 to maintain the diaper 20 about the waist of the wearer. The attachment panel 66 may include two separate panels located along the opposed side edges of the diaper 20 in one of the waist regions 22 and 24 of the diaper 20. Alternatively, the attachment panel 66 may include a single piece of material that extends substantially across the respective waist region of the diaper 20. In this configuration, the attachment panel 66 located on the outer cover 42 may further extend beyond the side edges 30 of the diaper 20 and include a folded over portion to which the first engageable portion 61 of continuous fastener 60 is refastenably engaged to provide the prefastened refastenable side seams 68.

Suitable fasteners to provide the engageable portions of the continuous fastener 60 are well known to those skilled in the art and can include adhesive tape tab fasteners, hook and loop fasteners, mushroom fasteners, snaps, pins, belts and the like, and combinations thereof. For example, as representatively illustrated in FIGS. 3, 4 and 6, the fasteners 60 may include hook type fasteners and the outer cover 42 may be configured to function as a complimentary loop type fastener. Alternatively, attachment panel 66 may be provided on the diaper 20 to function as a complementary loop type fastener. Desirably, the waist size adjustment means of the fasteners 60 are hook type fasteners which are releasably engageable directly with the outer cover 42 of the diaper 20. Such an arrangement provides the ability to vary the size of the waist opening in very small increments over a wide range to fit the waist of the wearer. Similarly, it is desirable to have the refastenable side seams 68 be formed by the direct engagement of the first portion 61 of the continuous fasteners 60 to the interior or the exterior surfaces 34 and 36 of the diaper 20.

Figure 5A:
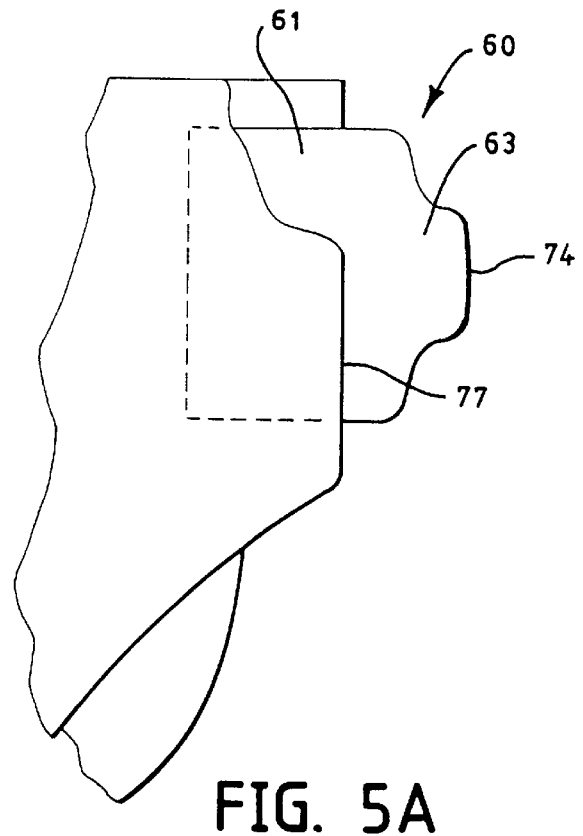
FIG. 5-A representatively shows a front plan view of an alternate configuration of the fastener of the absorbent article of FIG. 3, with portions of the article partially cut away to show underlying features.
Figure 5B:
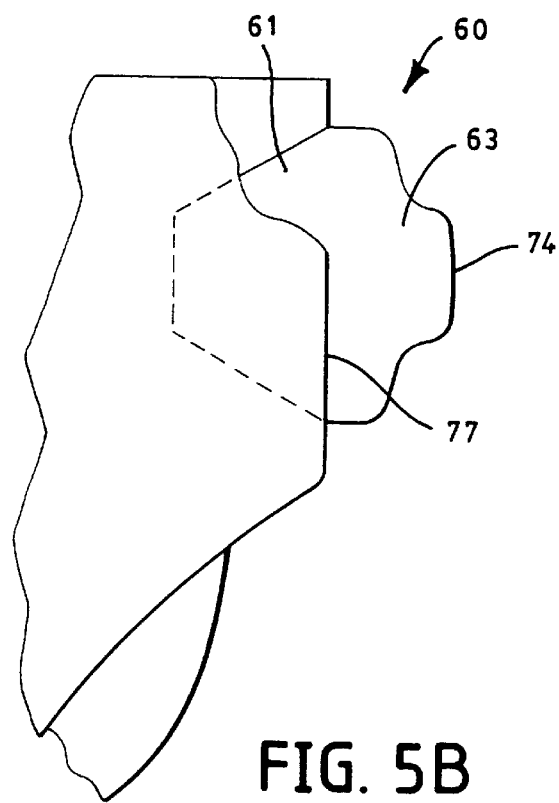

When the fastener 60 is comprised of a continuous fastening segment having first and second engageable portions 61 and 63 as illustrated in FIG. 3, the fastener 60 may consist of various shapes and sizes. For example, as representatively illustrated in FIGS. 5-A and 5-B, the first engageable portion 61 of the fastener 60 may provide a larger area than the second engageable portion 63 of the fastener 60. Conversely, the second engageable portion 63 of the fastener 60 may provide a larger area than the first engageable portion 61 of the fastener 60.

Moreover, as representatively illustrated in FIG. 3, the continuous fastener 60 of the present invention may include an inboard longitudinal edge 72, an outboard longitudinal edge 74, and an intermediate edge 77 that divides the first and second portions 61 and 63 of the continuous fastener 60. That is, the intermediate edge 77 is defined on the continuous fastener 60 as the edge where the fastener 60 protrudes laterally outward from the side seam 68. The intermediate edge 77 of the fastener 60 may define a length in the longitudinal direction 38 which is greater than either the length of the inboard longitudinal edge 72 or the outboard longitudinal edge 74 in the longitudinal direction. Desirably, as representatively illustrated in FIG. 5-A and 5-B, the intermediate edge 77 of the fastener 60 may be larger in the longitudinal direction 38 than both edges 72 and 74. As such, the larger intermediate edge 77 ensures that the first portion 61 of the fastener 60 is able to provide a longer side seam 68, affording improved fit and control of the leg and waist openings. In addition, as representatively illustrated in FIG. 5-B, by tapering the first portion of the fastener 60 in the inboard direction, the fastener 60 may still maintain a smaller fastening area toward the inboard longitudinal edge 72. As such, the smaller inboard longitudinal edge 72 of the continuous fastener 60 provides an improved sensation of comfort to the wearer by enhancing the wearer's freedom of leg movement. Further, the longitudinally larger intermediate edge 77 of the continuous fastener 60 provides improved attachment strength of the waist size adjustment means in use when it is engaged to the exterior surface 36 of the diaper 20.

The lateral width of the different portions 61 and 63 of the fastener 60 may not be of equal size. Desirably, the lateral width 78 of the first portion 61 of the continuous fastener 60 may be greater in the lateral direction 40 than the lateral width 79 of the second portion 63 of the continuous fastener 60. The fastener 60 in such a configuration advantageously provides a larger refastenable side seam 68, thereby improving the security of the side seam 68, particularly when the fastener is being pulled on or off the hips of the wearer. In addition, the continuous fastener 60 thusly configured provides a waist size adjustment means which may be more easily, peelingly, adjusted by the wearer or caregiver.

The continuous fastener 60 of the present invention may also include a fastener substrate 84 to which the continuous fastener 60 is attached. The fastener substrate 84 may be advantageously comprised of different materials. For example, the fastener substrate 84 may consist of an extensible or elastomeric panel. In such configurations, the substrate of the continuous fastener 60 provides improved fit and comfort to the wearer by allowing the continuous fastener 60 more flexibility and range in engaging the exterior surface 36 of the diaper 20. The fastener substrate 84 may be comprised of material well known in the art. The materials may include a stretch-bonded-laminate (SBL) material, a neck-bonded-laminate (NBL) material, an elastomeric film, an elastomeric foam material, or the like such as described above as being suitable for the fit panel 48. The fastener substrate 84 may alternately be provided by a substantially non-elastomeric material, such as polymer films, woven fabrics, non-woven fabrics, or the like such as described above as being suitable for the outer cover 42 or the bodyside liner 44.

In yet another alternative, the intermediate edge 77 of the continuous fastener 60 of the present invention may be advantageously comprised of a hinge. As such, the fastener 60 would desirably be thinner at the intermediate edge 77, and therefore easier to flex, thereby improving the attachment of the waist size adjustment means to the exterior surface 36 of the diaper 20. For example, the continuous fastener 60 may be mechanically pressed or rolled at the intermediate edge 77 to produce a fastener 60 that is thinner at the intermediate edge 77.

As set forth above, at least one of the fasteners 60 of the diaper 20 of the present invention may include a continuous fastener which provides both the prefastened, refastenable side seam 68 and the waist size adjustment means. As such, the use of fasteners which provide both the side seam 68 and a waist size adjustment means with one continuous fastening segment advantageously allows for ease of manufacturing, and a reduction of manufacturing costs resulting from a reduction of raw material usage. Alternatively, the fastener 60 may include separate fastening mechanisms which separately provide refastenable side seams 68 and the waist size adjustment means. For example, the fasteners 60 may be provided by separate fastening mechanisms, such as the primary 62 and secondary fasteners 64 illustrated in FIGS. 6–6C.

Figure 6:
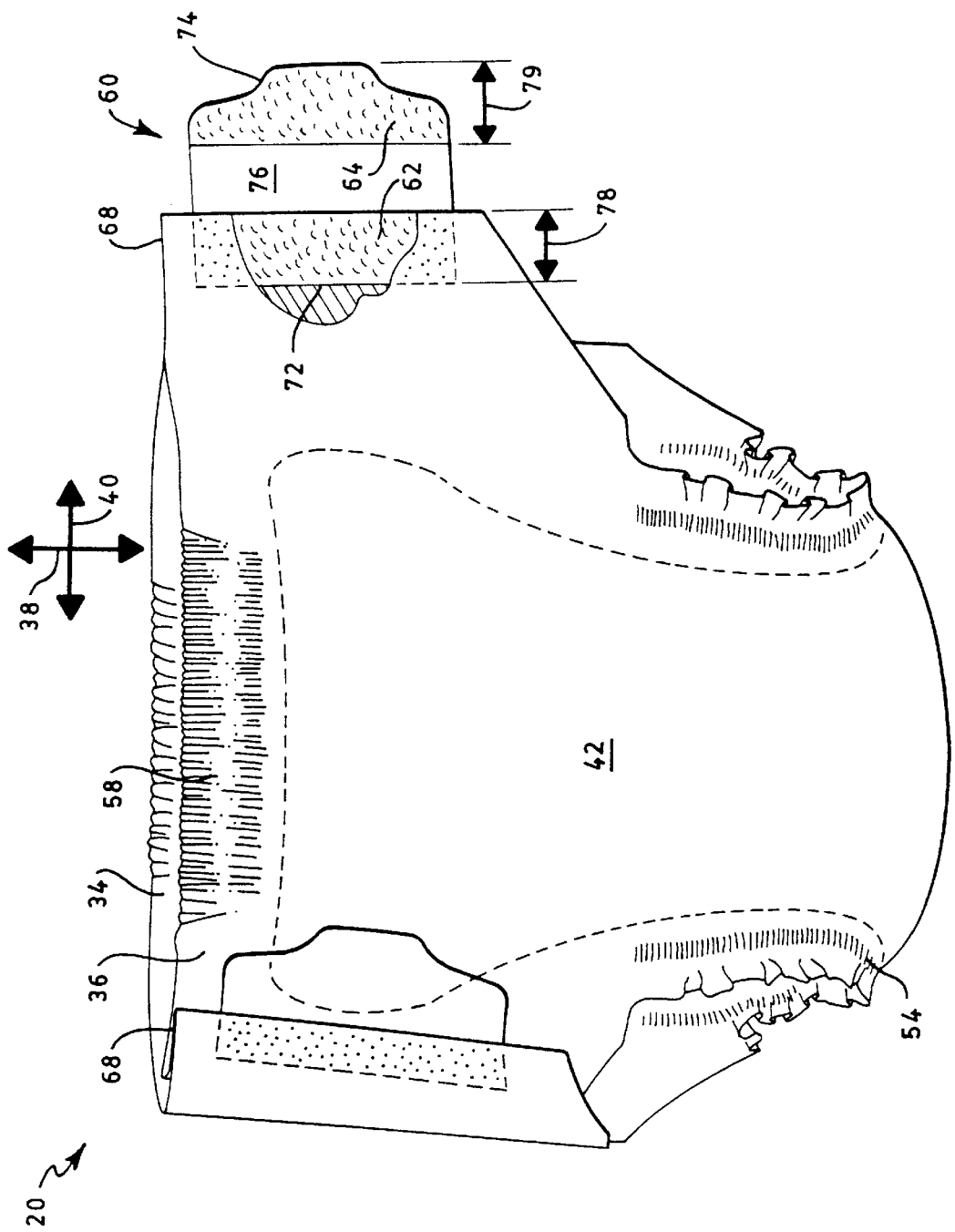
FIG. 6 representatively shows a front plan view of another example of a prefastened absorbent article of the present invention with one of the waist size adjustment means of the fasteners in the unengaged position and with portions of the article partially cut away to show the underlying features.
Figure 6A:
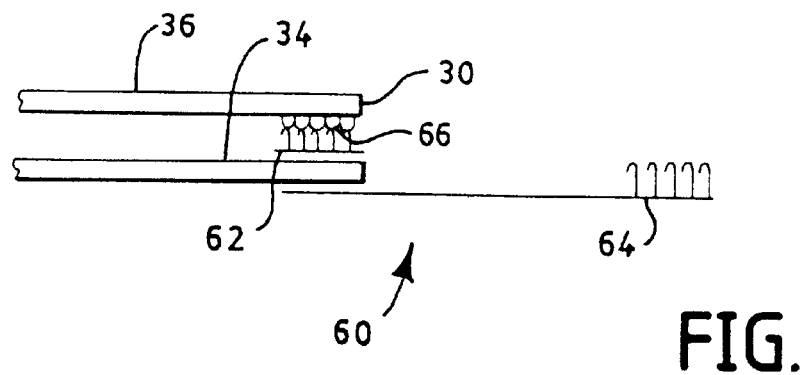
Figure 6B:
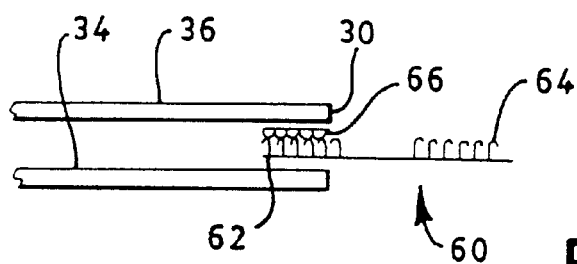
Figure 6C:
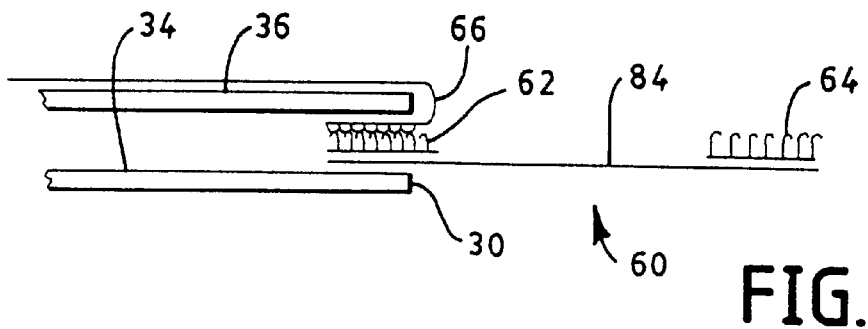

As representatively illustrated in FIG. 6, the fasteners 60 may include a pair primary fasteners 62, and a waist size adjustment means such as a pair of secondary fasteners 64. The primary fasteners 62 may be permanently attached to the laterally opposed side edges 30 in one of the waist regions 22 and 24 of the diaper 20 and refastenably attached to the side edges in the opposite waist region to provide the refastenable side seams 68.

As representatively illustrated in FIG. 6, the waist size adjustment means may be provided by a pair of secondary fasteners 64 that extend from the refastenable side seams 68. The secondary fasteners 64 may be located on the side edges 30 of the diaper 20 in the back waist region 24 of the diaper 20. As such, the secondary fasteners 64 are configured to encircle the hips of the wearer and engage the exterior surface 36 of the front waist region 22 of the diaper 20 to reduce the waist perimeter dimension of the waist opening and conform the waist of the diaper 20 on the wearer. Alternatively, the secondary fasteners 64 may be located on the front waist region 22 and may be configured to releasably engage the exterior surface 36 of the back waist region 24 of the diaper 20. In yet another alternative configuration, the diaper may include a single secondary fastener 64 extending from one of the refastenable side seams 68.

The multiple engaging portions 62 and 64 of the fastener 60 may be configured in multiple ways. For example, as representatively illustrated in FIG. 6-A, the secondary fastener 64 may be permanently attached to the exterior surface 36 of the waist region 22 and 24. At the same time the primary fastener 62 may be permanently attached to the interior surface 34 of the same waist region 22 and 24. Such a configuration can provide improved manufacturing efficiency.

Alternatively, as representatively illustrated in FIG. 6-B, the primary fastener 62 and the secondary fastener 64 may be assembled onto a single substrate to provide the fastener 60. This arrangement provides the advantages of the multiple fastener system, but with minimal use of additional materials, thereby providing cost savings. In addition, the minimal use of materials advantageously results in a cost savings as well as reduces the thickness of the fastener 60 and, as a result, increases the flexibility of the fastener thereby reducing irritation to the wearer. This configuration may further result in improved manufacturing efficiency through the use of nested patterns.

In yet another alternative, as representatively illustrated in FIG. 6-C, the primary fastener 62 and the secondary fastener 64 may both be permanently attached to the interior surface 34 of the waist region 22 and 24. As such, in this arrangement, the fastener 60 may advantageously be produced off line, thereby facilitating the manufacturing process and reducing manufacturing costs.

As representatively illustrated in FIG. 6, the fasteners 60, when configured with multiple engaging portions, may include an intermediate portion 76 between the primary 62 and secondary 64 fasteners. The intermediate portion 76 of the fastener 60 may be advantageously comprised of different materials. The intermediate portion 76 of the fastener 60 may consist of an extensible panel to which the first and second portions of the fastener 60 are attached. Thus, the extensible panel would provide improved fit and comfort to the wearer by allowing the fastener 60 more flexibility and range in engaging the exterior surface 36 of the diaper 20.

The extensible panel may be comprised of material well known in the art. The materials may include a stretch-bonded-laminate (SBL) material, a neck-bonded-laminate (NBL) material, an elastomeric film, an elastomeric foam material, or the like such as described above as being suitable for the fit panel 48. The intermediate portion 76 may alternately be provided by a substantially non-elastomeric material, such as polymer films, woven fabrics, non-woven fabrics, or the like such as described above as being suitable for the outer cover 42 or the bodyside liner 44.

In yet another alternative, the intermediate portion 76 of the fastener 60 of the present invention may be advantageously comprised of a hinge to which the primary and secondary fasteners 62 and 64 of the fastener 60 are attached. When the intermediate portion 76 of the fastener 60 is configured as a hinge, the fastener 60 would desirably be thinner at the intermediate portion 76, and therefore easier to flex for attachment of the secondary fastener 64 to the exterior surface 36 of the diaper 20. For example, the intermediate portion may consist of the fastener substrate 84.

The prefastened, refastenable side seams 68, which may include passive bonds 70, are configured to maintain the diaper 20 in a prefastened configuration as it is pulled on and off over the hips of the wearer and during use. Thus, it is desirable that the prefastened refastenable side seams 68 provide adequate shear strength for maintaining the diaper 20 in the prefastened configuration. Such strengths are well known to those skilled in the art. Similarly, the waist size adjustment means, which may include the second engageable portion 63 of the continuous fastener 60 or the secondary fastener 64, should provide adequate shear strength and peel strength to maintain engagement with the exterior surface 36 of the diaper 20.

The side seams 68 are also configured to be readily broken such that the caregiver can easily peelingly disengage the waist regions 22 and 24 to remove the diaper 20 from the wearer after it has been soiled, to inspect the diaper for soiling or to initially position the diaper 20 on the wearer if desired. Thus, it is desirable that the side seams 68 define a relatively low peel strength such that the caregiver can readily disengage the side seams 68 and break the passive bonds 70 to separate the waist region 22 and 24 to remove the diaper 20 from the waist of the wearer similar to conventional diapers which are not prefastened. Similarly, the waist size adjustment means which may include the second engageable portion 63 of the fastener 60 or the secondary fastener 64, are also configured to be readily broken such that the caregiver or the wearer can easily, peelingly disengage the waist size adjustment means from the exterior surface 36 of the diaper 20. This allows for the repositioning of the diaper 20 about the hips of the wearer, or for inspection of the diaper 20 without disengaging the side seams 68. Thus, it is desirable that the waist size adjustment means define a relatively low peel strength such that the caregiver can readily disengage the waist size adjustment means from the exterior surface 36 of the diaper 20. Suitable peel strength values are well known to those skilled in the art.

The different aspects of the present invention advantageously provide pant-like, prefastened, disposable absorbent articles that include refastenable side seams which also provide a waist size adjustment means. The benefits of the present invention may be provided by a single continuous fastener 60 which provides both the side seam 68 and a waist size adjustment means with one fastening segment thereby advantageously simplifying the manufacturing process and reducing raw material requirements, resulting in reduced manufacturing costs. Alternatively, the benefits may be provided by multiple fastening segments which may include a primary fastener and a secondary fastener.

The side seams of the present invention are prefastened to refastenably join the front and back waist portions providing a pant-like absorbent article. This configuration allows the absorbent article to be pulled up or down over the hips of the wearer such as conventional training pants. The refastenable side seams may include passive bonds which assist in maintaining the article in a prefastened condition as the article is pulled up or down over the hips of the wearer. Furthermore, the refastenable side seams prevent movement and shifting of the waist portions relative to each other for improved fit and performance. The refastenable side seams also prevent the rollover or folding in of the side and waist edges of the prefastened absorbent article as it is pulled over the wearer's hips.

Moreover, the waist size adjustment means furnishes a mechanism to reduce the waist perimeter dimension which better maintains the absorbent article about the waist of the wearer after the article has been positioned about the hips of the wearer. The waist size adjustment means is intended to maintain the diaper 20 in a close conforming fit about the waist of the wearer to reduce the leakage of body exudates when in use. The waist size adjustment means may also be selectively disengaged to facilitate inspection of the diaper 20 to determine if it has been soiled. The refastenable side seams 68 can also provide a "childproofing function" by maintaining the diaper 20 at least partially secured about the waist of the wearer if the wearer disengages the waist size adjustment means. The use of such a waist size adjustment means has been found to be particularly desirable when the refastenable side seams 68 are releasably engaged to provide a prefastened diaper which can be pulled on over the legs and hips of the wearer. As such, the waist opening of the diaper 20 must be sufficient to allow the prefastened diaper to be pulled over the hips of the wearer. However, the circumference of the waist of the wearer is typically less than the circumference around the hips of the wearer. Thus, the waist opening of the prefastened diaper may not conform to the waist of the wearer, which may undesirably result in leaks. Hence, the waist size adjustment means of the diaper 20 is configured to conform the waist regions of the diaper 20 to the wearer after the prefastened diaper is pulled on the wearer. Thus, the caregiver is not required to reposition the refastenable side seams to conform the waist regions 22 and 24 to the waist of the wearer. Therefore, when the diaper 20 is to be removed from the wearer, the care giver may simply disengage the waist size adjustment means if necessary and pull the prefastened diaper down over the hips and legs of the wearer without having to reposition the refastenable side seam 68.

As a result, the absorbent articles of the present invention are designed to conform to the body of the wearer to effectively contain bodily exudates while still being capable of being reliably pulled up or down over the hips of the wearer to assist in the toilet training of the wearer. Moreover, similar to conventional diapers, the absorbent articles of the present invention can advantageously be applied to and removed from the wearer with relative ease and cleanliness.

The methods of the different aspects of the present invention are directed at reliably and consistently providing the pant-like, refastenable disposable absorbent articles described herein such as those representatively illustrated in FIGS. 1–4, and 6. For example, the methods can include providing a continuous web of interconnected absorbent chassis. In such a configuration, the front waist region of the leading chassis may be connected to the back waist region of the trailing chassis to form the continuous web of interconnected absorbent chassis. Alternatively, the back waist region of the leading chassis may be connected to the back waist region of the trailing chassis or the chassis may be arranged in a front-to-front/back-to-back relationship.

The continuous web of interconnected absorbent chassis may be provided by means known to those skilled in the art. For example, a web of interconnected absorbent chassis, may be provided by intermittently placing individual absorbents 28 between a continuously moving web of outer cover material and a continuously moving web of bodyside liner material at spaced apart locations. Additional components, such as the leg elastics 54, containment flaps 56 and waist elastics 58, may also be connected to the continuously moving web of interconnected absorbent chassis. The different components of the diaper 20 may be connected together by means known to those skilled in the art such as, for example, adhesive, thermal or ultrasonic bonding. Desirably, most of the components are connected using ultrasonic bonding for improved manufacturing efficiency and reduced raw material cost.

A pair of laterally opposed fasteners 60 is also permanently attached to the side edges of the continuously moving web of interconnected absorbent chassis. For example, as representatively illustrated in FIGS. 1–4, and 6, the fasteners 60 are permanently attached to the side edges 30 of the back waist region 24 and are configured to refastenably engage with the front waist region 22 of the diaper 20 to provide a pair of refastenable side seams 68. Alternatively, the fasteners 60 may be located on the side edges 30 of the front waist region 22 of the diaper and in such a configuration the fasteners 60 are configured to refastenably engage with the back waist region 24 of the diaper 20 to provide a pair of refastenable side seams 68.

The fasteners 60 can be provided by unwinding a roll of fastener material, passing the web of fastener material through a die cutter which selectively cuts the web of fastener material into two webs of spaced apart fastener material. The individual fasteners 60 may then be provided by passing the webs of fastener material through a slip cutter and bonder which intermittently cut the respective webs of fastener material into discrete fasteners 60 and bond the fasteners 60 to the side edges 30 of the web of absorbent chassis at spaced apart locations. The slip cutter provides the spacing between the fasteners 60 by transferring the individual fasteners away from the slip cutter at a higher speed than the speed at which the webs of fastener material are provided to the slip cutter.

Suitable bonding equipment which can be used to provide the ultrasonic bonds is well known to those skilled in the art. Desirably, the bonder is an ultrasonic bonder for improved efficiency and cost effectiveness. For example, the bonder may include the combination of one or more rotary ultrasonic horns and an anvil roll between which the webs to be bonded are passed to provide the bonds. Suitable rotary ultrasonic horns are described in U.S. Pat. No. 5,90,403 to Ehlert, the disclosure of which is hereby incorporated by reference. Such rotary ultrasonic horns generally have a diameter of from about 5 to about 20 centimeters and a width of from about 2 to about 15 centimeters. Alternatively, the ultrasonic horn may be a stationary ultrasonic horn as are also known to those skilled in the art. Other suitable ultrasonic horns and ultrasonic bonders are commercially available from Branson Sonic Power Company, a business having offices in Danbury, Conn. The bonder could otherwise be a thermal or adhesive bonder as are known to those skilled in the art.

The bonder may be configured to provide the desired bonds in a variety of patterns and shapes or sizes. For example, the bonds may be provided as a pattern of points, dots, circles, squares, triangles and the like which may be arranged in a linear or nonlinear configuration. In the illustrated embodiments, such patterns may be located on the bonding horn or the anvil roll. Desirably, the pattern is located on the anvil roll for improved manufacturing efficiency.

The continuous web of interconnected absorbent chassis is then passed through a cutter which selectively cuts the web into discrete, individual diapers 20. Such cutters are generally known to those skilled in the art and may include, for example, the combination of a cutting roll and anvil roll through which the web travels. The anvil roll may include a hardened steel rotating roll while the cutting roll may include one or more flexible hardened steel blades clamped on to another rotating roll. The pinching force between the blade on the cutting roll and the anvil roll creates the cut. The cutting roll may have one or more blades depending upon the desired distance between the cuts.

The discrete diapers 20 are then folded in a conventional blade folder about a fold line extending in a lateral direction through the crotch region 26 of the diaper 20. As such, the waist regions 22 and 24 of each diaper are positioned in a facing relationship with the edges of the fasteners 60 in each waist region extending laterally outward beyond the side edges 30 of the diaper 20 as illustrated in FIGS. 1–3, and 6. The fold line extends in a lateral direction through the crotch region 26 of the diaper 20. Desirably, each diaper 20 is consistently folded about fold line such that the waist edges 32 of the diaper 20 in the front and back waist region 22 and 24 align with each other.

Suitable blade folders to provide the folding are well known to those skilled in the art. For example, the blade folder may include a pair of rotating folding blades which are configured to contact the diaper 20 along the fold line. In such a configuration, the rotation of the folding blades forces the diaper into a nip between two rotating rolls causing the diaper 20 to fold about the fold line.

The first portion of the fasteners 60 located on the side edges 30 of the back waist region 24, are then refastenably engaged with the front waist region of each diaper 20 to provide the refastenable side seam 68. The refastenable engagement of the opposed waist regions 22 and 24 may be ensured by rolling the refastenable side seam 68 between a pair of rotating nip rolls (not shown) which apply pressure to the opposed side edges 30 of the waist regions 22 and 24. Alternatively, applying a non-rolling, mechanical pressure to the refastenable side seam 68 may similarly ensure the refastenable engagement of the waist regions 22 and 24 with each other. The engagement of the fasteners in the side seams 68 may otherwise be enhanced at specific pressure points. For example, the side seams 68 may be enhanced by subjecting the seams 68 to a pattern of ultrasonic point bonds which ensure adequate engagement and increase the peel and shear strength of the side seams.

The waist regions 22 and 24 may also include passive bonds to further ensure their engagement of one to the other to form the refastenable side seam 68. The passive bonds 70 assist the fasteners 60 in maintaining the back waist region 22 refastenably attached to the front waist region 24 of the diaper 20. Such passive bonds 70 may be provided by passing the folded prefastened absorbent article through a bonder. Desirably, the bonder is also an ultrasonic bonder for improved efficiency and cost effectiveness. Suitable bonders for passively bonding the side seams 68 are described above. Suitable bond patterns are also described above.

The term "passive bond" as used herein refers to a bond which has a relatively low peel strength such that the bond can be broken by the caregiver if desired to assist in inspecting or removing the diaper 20 from the wearer without tearing or severely damaging the other portions of the diaper 20. The passive bonds may otherwise be broken prior to applying the diaper 20 to the wearer if it is desired to apply the pant-like, refastenable diaper of the present invention in a similar manner to conventional diapers.

The fasteners 60, which provide the refastenable side seams 68, also include a waist size adjustment means. For example, a second portion of the continuous fastener 60 may be configured to be releasably engage the exterior surface 36 of the diaper 20 to reduce the waist opening after the diaper 20 is positioned on a wearer. The waist size adjustment means may then be releasably engaged to the exterior surface 36 of the diaper 20 by first diverging the prefastened diaper 20 at the waist opening. For example, this can be achieved by a set of diverging vacuum conveyors. The side seams 68 are then directed inward in the lateral direction by suitable means as well known to those skilled in the art. Desirably, this may be accomplished with another set of blade folders as previously described herein. Finally, the diaper 20 is converged at the waist opening thereby refastenably attaching the second portion of the continuous fastener 60 to the exterior surface 36 of the diaper 20.

Alternatively, the waist size adjustment means may be releasably attached to the exterior surface 36 of the diaper 20 by directing the second portions of the fasteners 60 inward in the lateral direction about the refastenable side seams 68 of the diaper 20. The means of directing the second portion of the fastener 60 inward are generally well known to those skilled in the art. For example, a folding board may be used, through which the diaper 20 travels to direct the second portion of the primary fastener 60 inward and onto the exterior surface 36 of the diaper 20.

The methods of the present invention can reliably and consistently provide pant-like, refastenable absorbent articles such as the diaper illustrated in FIGS. 1–4, and 6.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A pant-like, prefastened, disposable absorbent article which defines an absorbent, a front waist region, a back waist region, a crotch region which extends between and connects said waist regions, a longitudinal direction, a lateral direction, an exterior surface, an interior surface opposite said exterior surface, a pair of laterally opposed side edges and a pair of longitudinally opposed waist edges, said absorbent article comprising:

a pair of continuous fasteners permanently attached to said laterally opposed side edges in one of said waist regions, wherein each of said continuous fasteners defines an inboard longitudinal edge and an outboard longitudinal edge and includes a first engageable portion which is refastenably attached to said side edges in an opposite waist region thereby providing a pair of refastenable side seams joining said waist regions together to define a waist opening having a waist perimeter dimension and a pair of leg openings and provide said prefastened absorbent article, wherein at least one of said continuous fasteners includes a second engageable portion which extends from one of said refastenable side seams and which is configured to releasably engage said exterior surface of said prefastened absorbent article to reduce said waist perimeter dimension and assist in maintaining said prefastened absorbent article about a wearer's hips after said prefastened absorbent article is positioned on a wearer.

2. The prefastened absorbent article according to claim 1 wherein said continuous fasteners are hook and loop type fasteners.

3. The prefastened absorbent article according to claim 1 and further comprising an outer cover that provides said exterior surface and wherein said outer cover is an elastomeric material.

4. The prefastened absorbent article according to claim 1 and further comprising an outer cover that provides said exterior surface and wherein said outer cover is an extensible material.

5. The prefastened absorbent article according to claim 1 and further comprising at least one fit panel superimposed adjacent one of said waist edges.

6. The prefastened absorbent article according to claim 1 wherein said first engageable portions of said continuous fasteners are located on said interior surface in said one waist region and are refastenably attached to said exterior surface in said opposite waist region to provide said refastenable side seams.

7. The prefastened absorbent article according to claim 1 wherein said first engageable portions of said continuous fasteners are located on said exterior surface in said one waist region and are refastenably attached to said exterior surface in said opposite waist region to provide said refastenable side seams.

8. The prefastened absorbent article according to claim 1 herein said first engageable portions of said continuous fasteners are located on said interior surface in said one waist region and are refastenably attached to said interior surface in said opposite waist region to provide said refastenable side seams.

9. The prefastened absorbent article according to claim 1 wherein said at least one continuous fastener includes an intermediate edge between said first and said second engageable portions and said intermediate edge provides a hinge.

10. The prefastened absorbent article according to claim 1 wherein said continuous fasteners are permanently attached to an extensible substrate which is permanently attached to said side edges of said absorbent article.

11. The prefastened absorbent article according to claim 1 wherein said at least one continuous fastener includes an intermediate edge between said first and said second engageable portions which defines a length in said longitudinal direction which is greater than a length of said inboard longitudinal edge and said outboard longitudinal edge in said longitudinal direction.

12. The prefastened absorbent article according to claim 1 wherein said first engageable portion of said at least one continuous fastener defines a first portion lateral width in said lateral direction which is greater than a second portion lateral width of said second engageable portion of said at least one continuous fastener.

13. The prefastened absorbent article according to claim 1 wherein an area of said first engageable portion is larger than an area of said second engageable portion of said at least one continuous fastener.

14. The prefastened absorbent article according to claim 2 and further comprising an outer cover which provides said exterior surface wherein said second engageable portion of said at least one continuous fastener is configured to directly refastenably engage said outer cover.

15. The prefastened absorbent article according to claim 2 and further comprising at least one exterior surface attachment panel which is located on said exterior surface wherein said second engageable portion of said at least one continuous fastener is configured to refastenably engage said exterior surface attachment panel.

16. The prefastened absorbent article according to claim 2 and further comprising an attachment panel located on said interior surface in said opposite waist region adjacent each of said side edges wherein said first engageable portions of said continuous fasteners are refastenably engaged to said attachment panel to provide said refastenable side seams.

17. The prefastened absorbent article according to claim 15 wherein said exterior surface attachment panel extends laterally beyond said side edges of said absorbent article and includes a folded over portion wherein said first engageable portions of said continuous fasteners are refastenably engaged to said folded over portions to provide said refastenable side seams.

18. The prefastened absorbent article according to claim 3 wherein said outer cover is a neck bonded laminate material.

19. The prefastened absorbent article according to claim 5 wherein said fit panel is superimposed on said interior surface.

20. The prefastened absorbent article according to claim 5 wherein said fit panel is superimposed on said exterior surface.

21. The prefastened absorbent article according to claim 5 wherein said fit panel is an elastomeric material.

22. The prefastened absorbent article according to claim 5 wherein said fit panel is attached on said one waist region to which said continuous fasteners are permanently attached.

23. The prefastened absorbent article according to claim 19 wherein said fit panel retains a free edge located longitudinally inward from said waist edge and between said side edges.

24. The prefastened absorbent article according to claim 10 wherein said extensible substrate is a neck bonded laminate.

25. A pant-like, prefastened, disposable absorbent article which defines an absorbent, a front waist region, a back waist region, a crotch region which extends between and connects said waist regions, a longitudinal direction, a lateral direction, an exterior surface, an interior surface opposite said exterior surface, a pair of laterally opposed side edges, and a pair of longitudinally opposed waist edges, said absorbent article comprising:

a pair of fasteners permanently attached to each of said side edges in said back waist region, wherein each fastener includes a primary fastener, a secondary fastener, an inboard longitudinal edge, an outboard longitudinal edge, and an intermediate portion between said primary fastener and said secondary fastener, wherein said primary fasteners are refastenably attached to said side edges of said absorbent article in said front waist region to provide a pair of refastenable side seams thereby defining a waist opening having a waist perimeter dimension and a pair of leg openings in said prefastened absorbent article, wherein said secondary fasteners are configured to refastenably attach to said exterior surface of said absorbent article in said front waist region to reduce said waist perimeter dimension of said waist opening after said prefastened absorbent article is positioned on a wearer.

26. The prefastened absorbent article according to claim 25 wherein said fasteners include an extensible panel to which said primary fasteners and said secondary fasteners of said fasteners are attached.

27. The prefastened absorbent article according to claim 25 and further comprising an outer cover that provides said exterior surface and wherein said outer cover is a neck bonded laminate material.

28. The prefastened absorbent article according to claim 25 and further comprising an outer cover that provides said exterior surface and wherein said outer cover is an extensible material.

29. The prefastened absorbent article according to claim 25 and further comprising at least one elastomeric fit panel superposed adjacent said waist edge in said back waist region of said absorbent article, wherein said fasteners are permanently attached to said fit panel in said back waist region.

30. The prefastened absorbent article according to claim 25 wherein said intermediate portions of said fasteners provide a hinge region between said primary fasteners and said secondary fasteners.

31. The prefastened absorbent article according to claim 25 wherein said intermediate portions of said fasteners define a length in said longitudinal direction which is greater than a length of said inboard longitudinal edge and said outboard longitudinal edge in said longitudinal direction.

32. The prefastened absorbent article according to claim 25 wherein said primary fasteners define a first portion lateral width in said lateral direction which is greater than a said second portion lateral width in said lateral direction of said secondary fasteners.

33. The prefastened absorbent article according to claim 25 wherein an area of said primary fasteners is larger than an area of said secondary fasteners.

34. The prefastened absorbent article according to claim 25 wherein said primary and secondary fasteners are hook and loop type fasteners.

35. The prefastened absorbent article according to claim 26 wherein said extensible panel is a neck bonded laminate material.

36. A pant-like, prefastened, disposable absorbent article which defines an absorbent chassis, a front waist region, a back waist region, a crotch region which extends between and connects said waist regions, a longitudinal direction, a lateral direction, a pair of opposed side edges and a pair of opposed waist edges, wherein said pant-like disposable absorbent article is made by a process which comprises the steps of:

a) providing a continuous web of interconnected absorbent chassis;

b) permanently attaching a pair of laterally opposed fasteners to said side edges in said back waist region;

c) selectively cutting said continuous web of interconnected absorbent chassis into discrete absorbent articles;

d) folding each of said discrete absorbent articles about a fold line extending in a lateral direction through said crotch region of said article thereby positioning said front waist region and said back waist region in a facing relationship; and e) refastenably attaching a first portion of said fasteners in said back waist region to said opposed side edges in said front waist region to create a pair of side seams and to define a waist opening having a waist perimeter dimension and a pair of leg openings, wherein a second portion on at least one of fasteners is configured to refastenably attach to an exterior surface of said absorbent article in said front waist region to reduce said waist perimeter dimension of said waist opening after said prefastened absorbent article is positioned on a wearer.

37. The prefastened absorbent article of claim 36 wherein said fasteners are hook and loop type fasteners.

38. The prefastened absorbent article of claim 36 wherein said fasteners are adhesive type fasteners.

39. The prefastened absorbent article of claim 36 wherein said refastenably attaching step further comprises the step of mechanically pressing said side seam.

40. The prefastened absorbent article of claim 36 wherein said refastenably attaching step further comprises the step of ultrasonically bonding said front waist region to said back waist region adjacent said side seams.

41. The prefastened absorbent article of claim 36 wherein said process further comprises the steps of:
   a) diverging said prefastened absorbent article at said waist opening;
   b) directing both of said side seams and said second portion of said fasteners inward in said lateral direction; and
   c) converging said prefastened absorbent article at said waist opening thereby refastenably attaching said second portion of said at least one fastener to said exterior surface of said absorbent article.

42. The prefastened absorbent article of claim 36 wherein said process further comprises the step of directing said second portion of said at least one fastener inward in said lateral direction about said side seam such that said second portion of said at least one fastener engages said exterior surface of said absorbent article.

* * * * *